US007139610B2

United States Patent
Ferek-Petric

(10) Patent No.: US 7,139,610 B2
(45) Date of Patent: Nov. 21, 2006

(54) CAPTURE MANAGEMENT IN MULTI-SITE PACING

(75) Inventor: Bozlder Ferek-Petric, Zegreb (HR)

(73) Assignee: Medtronic, Inc., Minneapolis, MN (US)

( * ) Notice: Subject to any disclaimer, the term of this patent is extended or adjusted under 35 U.S.C. 154(b) by 451 days.

(21) Appl. No.: 10/132,510

(22) Filed: Apr. 26, 2002

(65) Prior Publication Data

US 2003/0204214 A1 Oct. 30, 2003

(51) Int. Cl.
*A61N 1/37* (2006.01)

(52) U.S. Cl. .................................... 607/27

(58) Field of Classification Search .............. 607/27, 607/28; 128/901
See application file for complete search history.

(56) References Cited

U.S. PATENT DOCUMENTS

| | | | | |
|---|---|---|---|---|
| 3,825,015 A | * | 7/1974 | Berkovits | 607/123 |
| 4,549,548 A | * | 10/1985 | Wittkampf et al. | 607/27 |
| 4,991,583 A | * | 2/1991 | Silvian | 607/13 |
| 5,003,975 A | * | 4/1991 | Hafelfinger et al. | 607/28 |
| 5,312,441 A | | 5/1994 | Mader et al. | |
| 5,331,966 A | * | 7/1994 | Bennett et al. | 600/508 |
| 5,411,524 A | | 5/1995 | Rahul | |
| 5,527,345 A | | 6/1996 | Infinger | |
| 5,584,868 A | | 12/1996 | Salo et al. | |
| 5,601,615 A | | 2/1997 | Markowitz et al. | |
| 5,626,620 A | * | 5/1997 | Kieval et al. | 607/9 |
| 5,741,312 A | * | 4/1998 | Vonk et al. | 607/28 |
| 5,797,967 A | | 8/1998 | KenKnight | |
| 6,148,234 A | | 11/2000 | Struble | |
| 6,163,724 A | | 12/2000 | Hemming et al. | |
| 6,324,425 B1 | * | 11/2001 | Blow et al. | 607/13 |
| 6,434,428 B1 | * | 8/2002 | Sloman et al. | 607/28 |
| 6,473,650 B1 | * | 10/2002 | Larsson et al. | 607/28 |
| 6,512,953 B1 | * | 1/2003 | Florio et al. | 607/28 |
| 6,640,136 B1 | * | 10/2003 | Helland et al. | 607/28 |
| 6,687,545 B1 | * | 2/2004 | Lu | 607/28 |
| 6,751,504 B1 | * | 6/2004 | Fishler | 607/25 |
| 6,782,291 B1 | * | 8/2004 | Bornzin et al. | 607/28 |

FOREIGN PATENT DOCUMENTS

EP 1 155 711 11/2001

* cited by examiner

*Primary Examiner*—George Manuel
*Assistant Examiner*—Lenwood Faulcon, Jr.
(74) *Attorney, Agent, or Firm*—Paul H. McDowall; Girma Wolde-Michael

(57) ABSTRACT

Methods and apparatus for capture management in multi-chamber pacing are disclosed. In one embodiment, the invention includes determining a combination of electrodes from a plurality of electrodes that yields the lowest polarization potential immediately following delivery of an electrical stimulus to a heart; and performing capture detection using that combination of electrodes. In order to distinguish loss of capture in one ventricle in bi-ventricular pacing, certain embodiments may also include measuring a width of a QRS complex and determining when the width is greater than a predetermined value. A method for detecting single ventricular loss of capture in bi-ventricular pacing is also described utilizing comparison of evoked QRS complex morphology to a predefined waveform.

22 Claims, 15 Drawing Sheets

CAPTURE MANAGEMENT IN MULTI-SITE PACING

FIELD OF THE INVENTION

The present invention relates to implantable medical devices such as implantable cardiac pacemakers and cardioverter/defibrillators. More particularly, the present invention pertains to implantable medical devices for use in multi-site pacing.

BACKGROUND OF THE INVENTION

Implantable medical devices (IMDs) for use in cardiac pacing and defibrillation are well known. Most of these devices include sense amplifier circuitry for detecting intrinsic cardiac electrical activity so that the devices may be inhibited from generating unnecessary stimulating pulses when a heart is functioning properly. While the present invention is not limited to any one IMD, it will, for the sake of brevity, be described with respect mainly to pacemaker-cardioverter-defibrillators (PCDs).

Dual-chamber cardiac pacemakers typically have separate sense amplifiers and associated circuitry for atrial and ventricular sensing. The sense amplifiers detect the presence of intrinsic signals, that is P-waves occurring naturally in the atrium and R-waves occurring naturally in the ventricle. Upon detecting an intrinsic signal, sense amplifier circuitry generates a signal for output to other components which then inhibits the delivery of a pacing pulse to the corresponding chamber.

It is desirable to accurately and reliably measure the response of the heart to an electrical stimulation pulse. Measuring such a response permits, among others, the determination of a patient's stimulation threshold, or the minimum energy a stimulating pulse must contain for a cardiac response to be evoked. Once a patient's stimulation threshold is determined, the energy content of stimulating pulses may be adjusted to avoid delivering pulses having unnecessarily high energy content. Minimizing the energy content of stimulating pulses is believed to have physiological benefits, and additionally reduces power consumption, a key concern in the context of battery-powered IMDs.

such capture detection and management is also useful in controlling a pacemaker's pacing rate, for ascertaining the physiological effect of drugs, or for diagnosing abnormal cardiac conditions. As used herein, the term "capture" means the successful evocation of a stimulated response in cardiac tissue by a pacing pulse. Capture is discussed in detail, for example, in U.S. Pat. No. 5,601,615 to Markowitz et al. and U.S. Pat. No. 6,163,724 to Hemming et al. "Loss of Capture" (or LOC) as used herein, indicates the failure to produce an evoked response.

Immediately following delivery of a pacing pulse to cardiac tissue, a residual post-pace polarization signal (or polarization potential) is produced by the charge induced in the tissue by the delivery of the pacing pulse. If the pacing pulse causes an evoked response in the cardiac tissue, then an evoked response signal is superimposed atop the typically larger amplitude polarization potential. As a result, conventional pacemakers either cannot differentiate, or have difficulty differentiating, between post-pacing pulse polarization potential and evoked response potential.

This problem is further complicated by the fact that residual polarization potentials typically have high amplitudes, even when an evoked response signal occurs. Consequently, it becomes difficult to detect an evoked response potential using a conventional pacemaker sense amplifier employing linear frequency filtering techniques.

Some pacemakers employ sensing and timing circuits that do not even attempt to detect evoked response potential until the polarization potential is no longer present or has subsided to some minimal amplitude level. With respect to capture detection, however, such sensing after the polarization potential is no longer present typically occurs a significant period of time after any evoked response signal has occurred. As a result, these pacemakers cannot reliably detect evoked response signals. Thus, a need exists for reliably determining whether or not an evoked response has occurred in a pacing environment.

Polarization signals typically arise due to the tissue-electrode interface storing energy after a pacing stimulus has been delivered. There are typically two tissue-electrode interfaces in a pacing circuit: one for the tip electrode, and one for the ring (or PCD housing) electrode. The stored energy dissipates after the pacing pulse is delivered, creating the subsequent polarization potential.

Another problem with capture management is peculiar in multi-site pacing, e.g., bi-ventricular pacing. In single ventricular pacing, the ventricular threshold may be determined by incrementally decreasing the pacemaker output until loss of capture is detected, either by human operator or by the pacemaker logic in the capture management function. This task is simplified by the fact that loss of ventricular response is easily detected by lack of an evoked QRS complex or wave following the pacing pulse, e.g., there is no cardiac contraction in response to the pacing pulse.

In bi-ventricular pacing, the task of the threshold measurement is somewhat more complicated. For instance, in most patients, the left ventricular threshold is higher than the right ventricular threshold (this holds true in spite of recent technological improvements in the design and configuration of left ventricular leads). Yet, the right ventricular pacing electrode typically has ideal contact with the endocardium. Therefore, it is believed to be more effective than electrodes located within the coronary vein that deliver the pacing pulse to the epicardium.

If bi-ventricular threshold detection is done in a manner similar to that described above with respect to single ventricle pacing, the incremental decrease of the left ventricular output will cause loss of capture (LOC) of the left ventricle as soon as the output falls below the left ventricular threshold. However, this will not be manifested in loss of the QRS complex (loss of the ventricular contraction) following the pacing pulse because the right ventricular pacing pulse continues to pace. That is, the depolarization wave will still occur, spreading from the right ventricle electrode implantation site, e.g., the apex of the right ventricle. In other words, while the evoked QRS complex morphology may change, it will still be present, indicating capture was detected.

Similarly, incrementally decreasing the right ventricular output will cause right ventricular LOC as soon as the output falls below the right ventricular threshold. Once again, this loss of capture will be not manifested in loss of the QRS complex following the pacing pulse because the left ventricular pacing pulse will continue to pace, producing a depolarization wave starting from the left ventricle electrode implantation site. As a result, the depolarization wave propagation will still be present. Thus, bi-ventricular capture management requires more that merely detecting the absence of the QRS complex.

The problems described herein above, e.g., threshold measurement and capture detection in view of polarization potential, may also present themselves in capture management for atrial pacing, e.g., in three and four chamber pacemakers.

Various methods have been proposed in the prior art for improving the ability to detect and measure evoked responses as well as improving other aspects of IMDs.

For example, U.S. Pat. No. 5,312,441 to Mader et al., discloses, in one embodiment, a method and apparatus for discriminating between ventricular depolarizations resulting from normal and abnormal propagation of the depolarization wave front through the ventricles by means of a measurement of a width of the sensed R-wave associated with the depolarization.

U.S. Pat. No. 5,797,967 to KenKnight, proposes an electrical therapy applied to a selected region of selected cardiac tissue, comprising the combination of two discrete therapies: pacing level therapy applied to a localized portion of a region of the selected cardiac tissue having relatively low susceptibility to defibrillation-level shock field strengths; followed by (or occurring simultaneously with) defibrillation therapy applied to portions of the tissue having regions of fibrillating myocardium over which the sub-defibrillation level shocks exert control.

U.S. Pat. No. 5,411,524 to Rahul describes a method and apparatus for synchronization of atrial defibrillation pulses. In one embodiment, a method and apparatus for controlling the timing of delivery of atrial cardioversion or defibrillation pulses is disclosed. In order to determine an appropriate time for delivery of a cardioversion pulse, the method and apparatus of the Rahul patent first determines the average V—V interval associated with the ventricular rhythm in the presence of atrial fibrillation. Based upon this average interval, the apparatus calculates a shorter, derived escape interval, which is used to control timing of delivery of the atrial cardioversion or defibrillation pulse.

U.S. Pat. No. 5,548,868 to Salo et al. proposes a cardiac stimulating apparatus and method. In particular, Salo et al. describes a cardiac defibrillator in combination with a pacing device with adjustable control of the AV interval.

U.S. Pat. No. 6,148,234 to Struble describes a dual site pacing system with automatic pulse output adjustment. In one embodiment, a dual site pacing system is provided with the capability of automatically detecting when there is LOC in one chamber, either ventricular or atrial. Following each delivered pair of pacing pulses to the dual sites, the pacemaker times out an appropriate blanking interval, and then times out a refractory period to coincide with the heart chamber's normal period of refractoriness following a contraction. During the refractory interval, or refractory period, the pacemaker looks to see if an excitation signal is sensed. If so, this means that a chamber was not captured, and the excitation from the other chamber (which was captured by a delivered pulse) had been conducted to the non-captured chamber.

Accordingly, various implementations of systems for capture management in multi-site pacing are known. These systems are described above and in the documents listed in Table I below.

TABLE I

| U.S. Pa. No. | Inventor | Issue Date |
| --- | --- | --- |
| 6,163,724 | Hemming et al. | Dec. 19, 2000 |
| 6,148,234 | Struble | Nov. 14, 2000 |
| 5,797,967 | KenKnight | Aug. 25, 1998 |
| 5,601,615 | Markowitz et al. | Feb. 11, 1997 |

TABLE I-continued

| U.S. Pa. No. | Inventor | Issue Date |
| --- | --- | --- |
| 5,584,868 | Salo et al. | Dec. 17, 1996 |
| 5,411,524 | Rahul | May 2, 1995 |
| 5,312,441 | Mader et al. | May 17, 1994 |

All documents listed in Table I herein above are hereby incorporated by reference in their respective entireties. As those of ordinary skill in the art will appreciate readily upon reading the Summary of the Invention, Detailed Description of the Embodiments, and claims set forth below, many of the devices and methods disclosed in the documents of Table I and others documents incorporated by reference herein may be modified advantageously by using the teachings of the present invention. However, the listing of any such document in Table I, or elsewhere herein, is by no means an indication that such documents are prior art to the present invention.

SUMMARY OF THE INVENTION

The present invention has certain objects. That is, various embodiments of the present invention provide solutions to one or more existing problems with respect to multi-site cardiac pacing. One such problem involves the need to more accurately discern polarization potential from evoked response polarization signals after delivery of a pacing pulse. Another problem involves the need to determine loss of capture of a single ventricle in bi-ventricular pacing systems.

In comparison to known multi-site cardiac pacing techniques, various embodiments of the present invention may provide one or more of the following advantages. For instance, pacing methodologies in accordance with embodiments of the present invention may select a sensing vector between two or more electrodes of a plurality of electrodes that records the lowest polarization potential. As a result, the evoked response signal indicative of capture detection is more pronounced. Further, devices and methods of the present invention may permit atrial capture detection across both atria by utilizing one or more electrodes normally used for delivering atrial or ventricular pacing pulses. Moreover, methods of the present invention permit discrimination of loss of capture of a single ventricle in bi-ventricular pacing systems.

Some embodiments of the present invention include a method for delivering therapy to a heart, having one or more of the following features: providing a plurality of electrodes in or around the heart; delivering an electrical stimulus to the heart; measuring a polarization potential vector between at least a first pair of electrodes of the plurality of electrodes and a second pair of electrodes of the plurality of electrodes; comparing the polarization potential vector between at least the first pair of electrodes and the second pair of electrodes; selecting a sensing pair of electrodes from at least the first pair of electrodes and the second pair of electrodes that yields the lowest polarization potential vector, where the sensing pair of electrodes is operable for use in sensing an evoked response of the heart to a subsequent electric stimulus delivered thereto; programming an implantable medical device to utilize the selected sensing pair of electrodes to sense the evoked response during capture management; implanting electrodes in select locations proximate one or more of a right ventricle, a right atrium, and a left lateral coronary vein of the heart, wherein implanting electrodes may include implanting a bipolar electrode proximate the right ventricle, implanting a bipolar electrode proximate the right atrium, and implanting a unipolar electrode proximate the left lateral coronary vein; delivering the electrical stimulus with one or more of the plurality of electrodes; and sensing the evoked response using the selected pair of sensing electrodes.

Another embodiment of a method for delivering therapy to a heart using an implantable medical device may include one or more of the following features: implanting a first lead of the implantable medical device proximate a right ventricle of the heart, the first lead having at least one electrode associated therewith; implanting a second lead of the implantable medical device proximate a right atrium of the heart, the second lead having at least one electrode associated therewith; implanting a third lead of the implantable medical device through a left lateral coronary vein of the heart proximate a left ventricle of the heart, the third lead having at least one electrode associated therewith; delivering an electrical stimulus to at least one chamber of the heart; measuring a polarization potential vector between each of a plurality of combinations of electrodes associated with the first lead, the second lead, the third lead, and a housing of the implantable medical device; comparing the measured polarization potential vector of each of the plurality of combinations of electrodes; selecting a combination of electrodes that yields the lowest measured polarization potential vector for the at least one chamber of the heart, wherein the selected combination of electrodes is operable for sensing an evoked response to a subsequent electric stimulus delivered to the at least one chamber of the heart; measuring the polarization potential vector between each of the plurality of combinations of electrodes by measuring two or more of the polarization potential vectors between: one or both of a cathode and an anode of the first lead and one or both of a cathode and an anode of the second lead, one or both of the cathode and the anode of the first lead and one or both of a cathode and an anode of the third lead, and one or both of the cathode and the anode of the second lead and one or both of the cathode and the anode of the third lead; detecting the evoked response in the at least one chamber of the heart using the selected combination of electrodes; delivering a pacing pulse to one or both of the right ventricle and the left ventricle; detecting the evoked response in one or both of the right ventricle and the left ventricle after delivering the pacing pulse; delivering the pacing pulse to the right ventricle via the at least one electrode associated with the first lead; delivering the pacing pulse to the left ventricle via the at least one electrode associated with the second lead; implanting the first lead proximate the right ventricle such that a tip electrode of the first lead contacts an interior surface of the right ventricle proximate an apex of the heart; implanting the second lead through a coronary sinus of the heart; and implanting one or more electrodes proximate a left atrium of the heart.

In yet another embodiment, a method of pacing one or both of a right atrium and a left atrium of a heart may include one or more of the following features: providing an implantable medical device having at least a first lead and a second lead, wherein the first lead comprises a first electrode at or near its distal end and the second lead comprises a second electrode at or near its distal end; locating the first electrode proximate a right atrium of the heart; locating the second electrode proximate a left side of the heart; delivering an atrial pacing pulse to one or both of the right atrium and the left atrium; detecting an evoked response of one or both of the right atrium and the left atrium by measuring an electrical potential vector between the first electrode and the second electrode; locating the second electrode proximate a left ventricle of the heart; pacing the left ventricle of the heart using at least the second electrode; implanting the second lead through a coronary sinus of the heart; delivering the atrial pacing pulse between the first electrode and a conductive portion of a housing of the implantable medical device; delivering the atrial pacing pulse between a tip electrode portion of the first electrode and a ring electrode portion of the first electrode; and detecting the evoked response immediately following delivery of the atrial pacing pulse.

In still yet another embodiment, an implantable medical device operable for pacing one or both of a right atrium and a left atrium of a heart may include one or more of the following features: a housing; an atrial pulse generator located within the housing; logic and control circuitry located within the housing and operable to control the atrial pulse generator; a first lead extending from the housing and having a first electrode at or near its distal end, the first electrode locatable proximate a right atrium of the heart; a second lead extending from the housing and having a second electrode at or near its distal end, the second electrode locatable proximate a left side of the heart; and sensor circuitry operable to sense an evoked response of the heart between the first electrode and the second electrode.

A method for bi-ventricular pacing of a heart using an implantable medical device is also provided and may include one or more of the following features: delivering a first electrical stimulus to a right ventricle; measuring a width of a first QRS complex; detecting that the width of the first QRS complex is greater than a first predetermined width; setting a magnitude of a first electrical output stimulus to the right ventricle; delivering a second electrical stimulus to a left ventricle; measuring a width of a second QRS complex; detecting that the width of the second QRS complex is greater than a second predetermined width; setting a magnitude of a second electrical output stimulus to the left ventricle; determining whether the first electrical output stimulus to the right ventricle is greater than a first threshold value, and disabling delivery of the first electrical output stimulus to the right ventricle; determining whether the second electrical output stimulus to the left ventricle is greater than a second threshold value, and disabling delivery of the second electrical output stimulus to the left ventricle; and issuing a patient alert.

A method for pacing a ventricle of a heart using an implantable medical device is also provided and may include one or more of the following features: selecting a combination of sensing electrodes from a plurality of electrodes that yields a lowest polarization potential vector in response to an electrical stimulus to the ventricle; delivering a pacing pulse to the ventricle; measuring one or more parameters of a QRS complex using the selected combination of sensing electrodes; detecting capture of the ventricle in response to the pacing pulse by comparing the one or more parameters of the QRS complex to one or more predetermined values; measuring a width of the QRS complex; and measuring a morphology of the QRS complex.

The above summary of the invention is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The present invention will be further described with reference to the drawings, wherein.

DETAILED DESCRIPTION OF THE PREFERRED EMBODIMENTS

Figure 1:
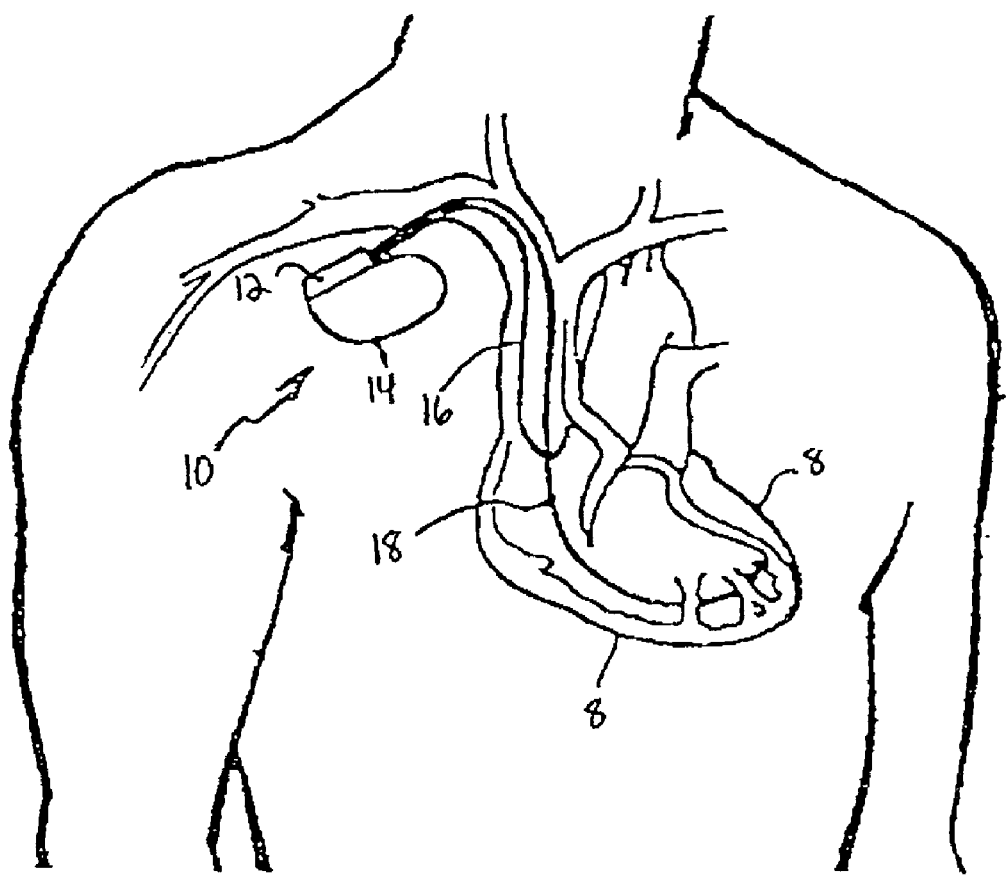
FIG. 1 is an implantable medical device (IMD) in accordance with one embodiment of the invention, wherein the IMD is implanted within a body of a patient.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18, sense electrical signals attendant to the depolarization and re-polarization of the heart 8, and further provide pacing pulses for causing depolarization of cardiac tissue in the vicinity of the distal ends thereof. Leads 16 and 18 may have, for example, unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson.

Figure 2:
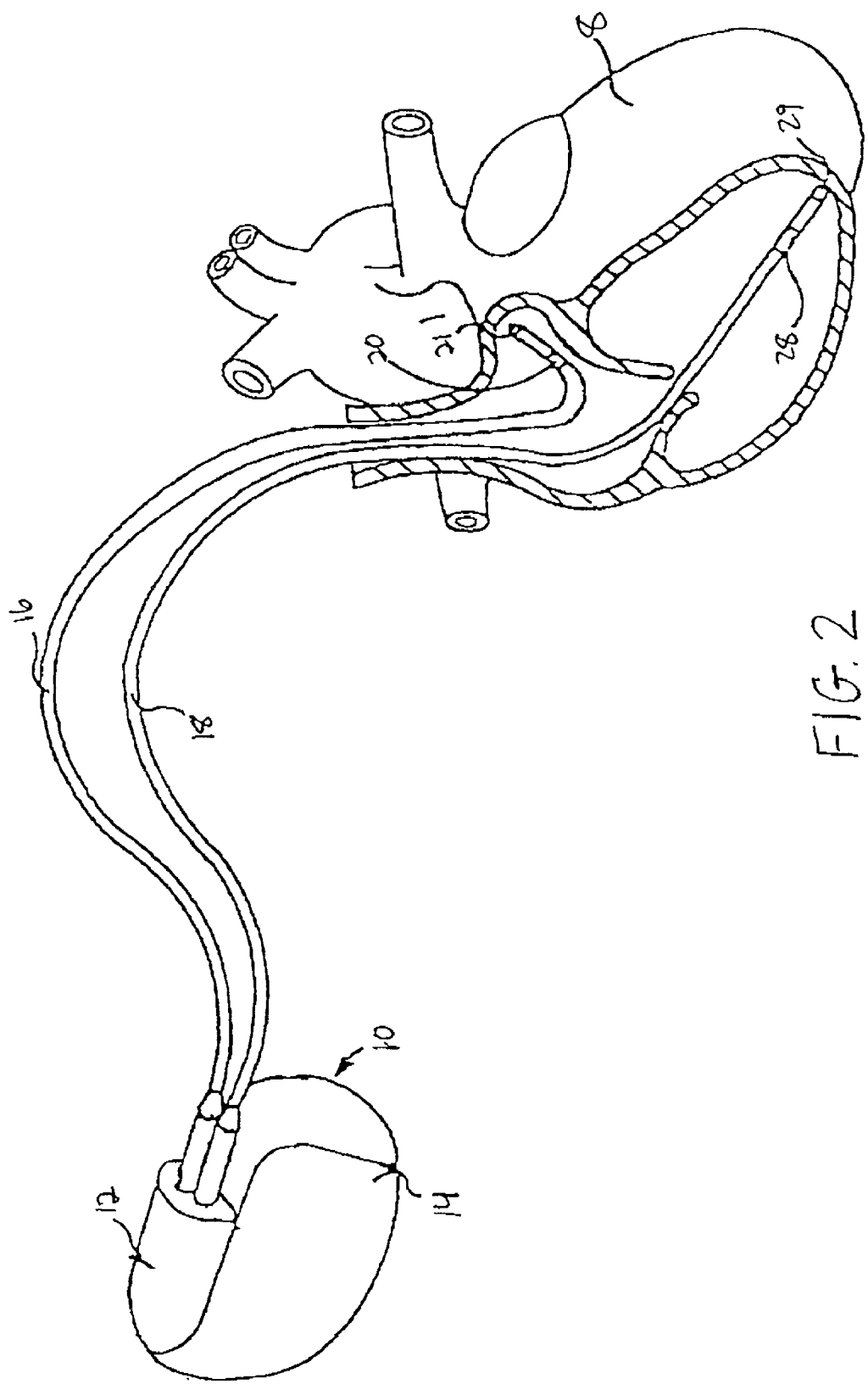
FIG. 2 is an enlarged view of the IMD of FIG. 1 diagrammatically illustrating coupling with the patient's heart in accordance with one embodiment of the invention.

FIG. 2 shows connector module 12 and hermetically sealed enclosure 14 of IMD 10 located near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
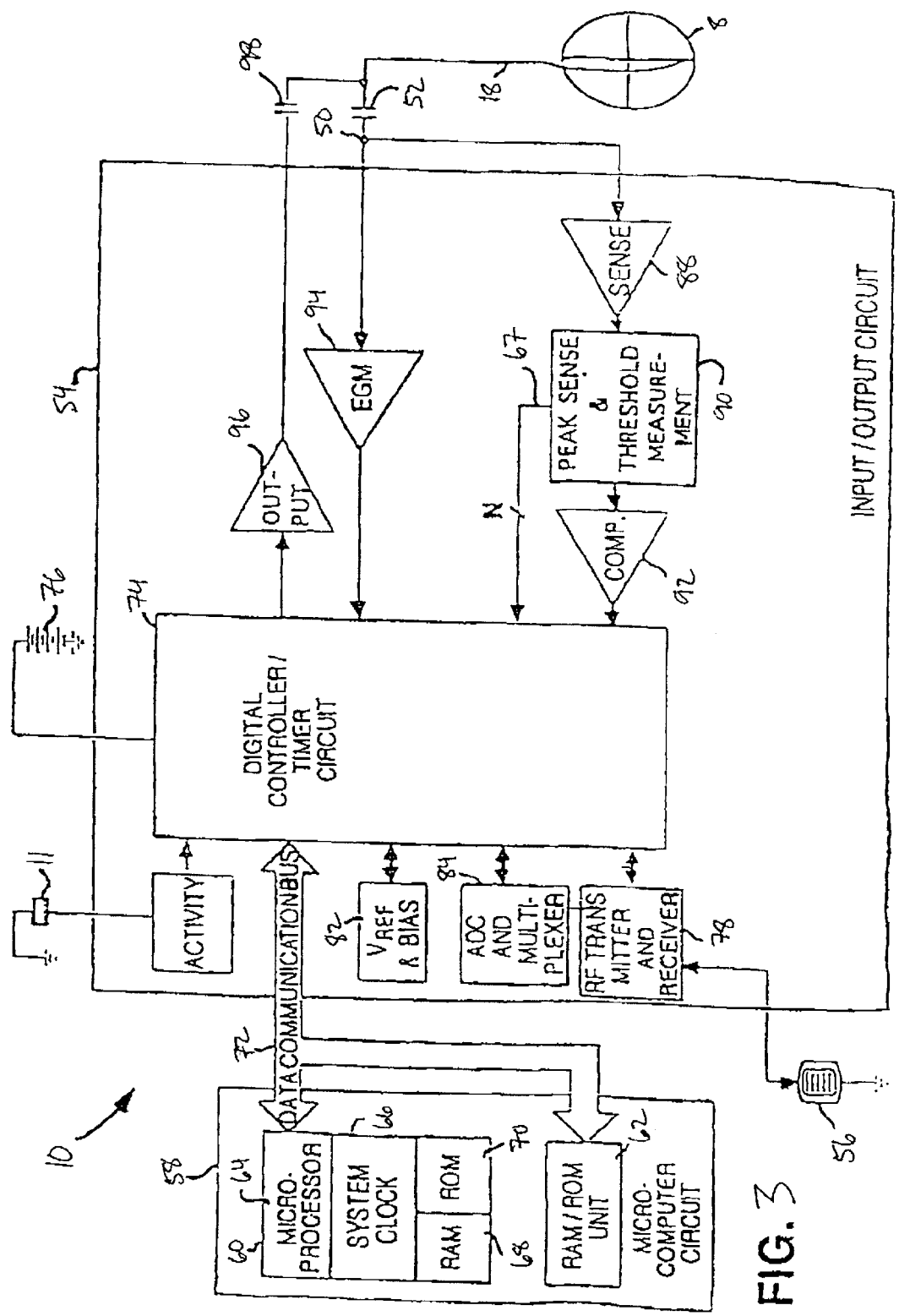
FIG. 3 is a functional block diagram of an IMD in accordance with one embodiment of the present invention.

FIG. 3 is a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,354,319 to Wyborny et al. The programming methodology disclosed in Wyborny et al.'s '319 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,556,063 issued to Thompson et al., or to that disclosed in the above-referenced '319 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

$V_{REF}$ and Bias circuit 82 (see FIG. 3) most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al. Output pulse generator 96 provides pacing stimuli to patient's heart 8 through coupling capacitor 98, for example, in response to a pacing trigger signal provided by digital controller/timer circuit 74 each time the escape interval times out, in response to an externally transmitted pacing command or in response to other stored commands as is well known in the pacing art. By way of example, output amplifier 96 may correspond generally to an output amplifier disclosed in U.S. Pat. No. 4,476,868 to Thompson.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

Various embodiments of the present invention may be practiced in conjunction with multiple-chamber pacemakers having two or more leads. At least some embodiments of the present invention may be applied equally well in the contexts of dual-, triple- or quadruple-chamber pacemakers or other types of IMD's for that matter (see e.g., U.S. Pat. No. 5,800,465 to Thompson et al.).

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker, Jr. et al.

Figure 4:
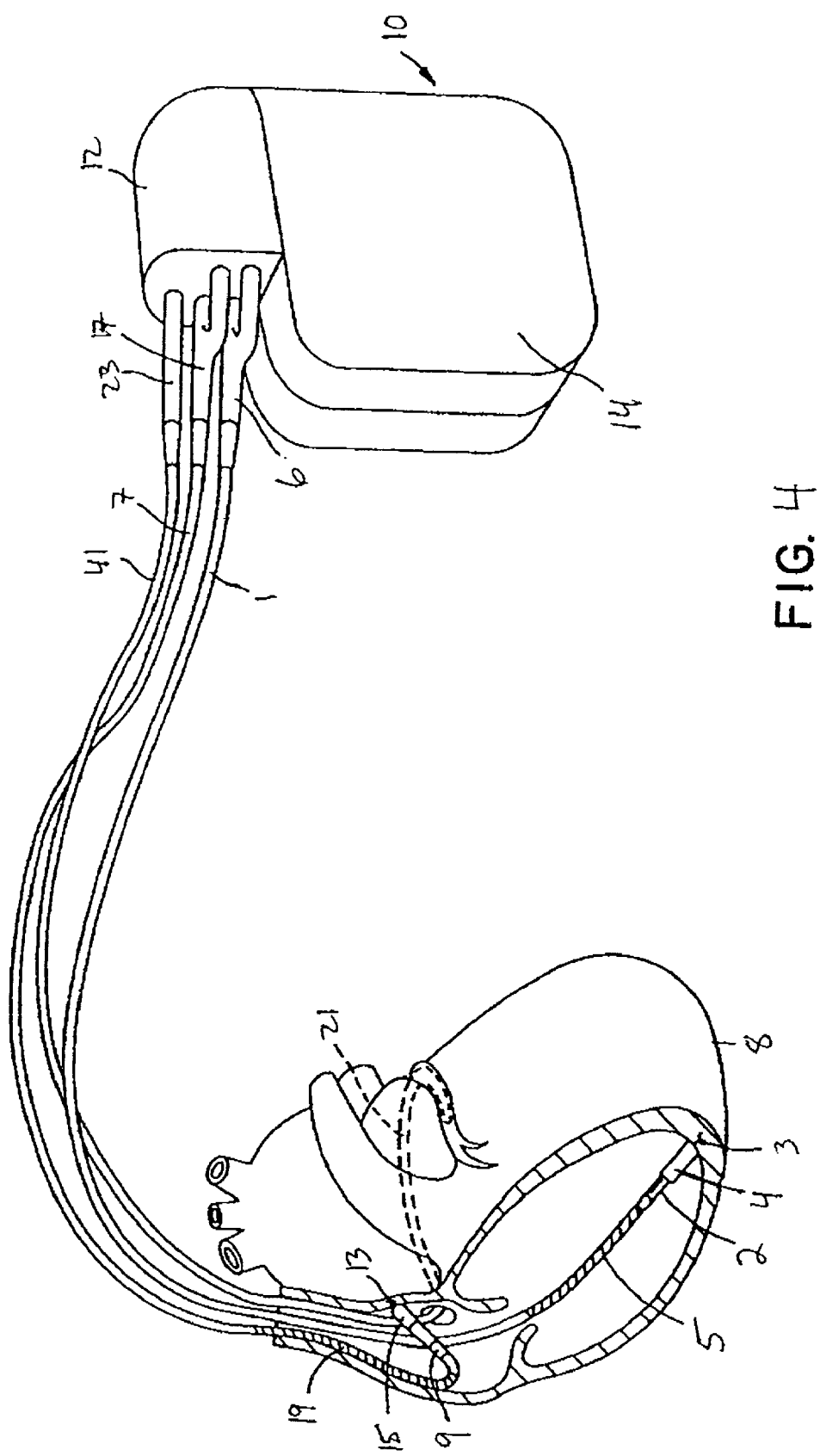
FIG. 4 is an IMD in accordance with another embodiment of the invention, wherein the IMD is an implantable pacemaker-cardioverter-defibrillator (PCD)
Figure 5:
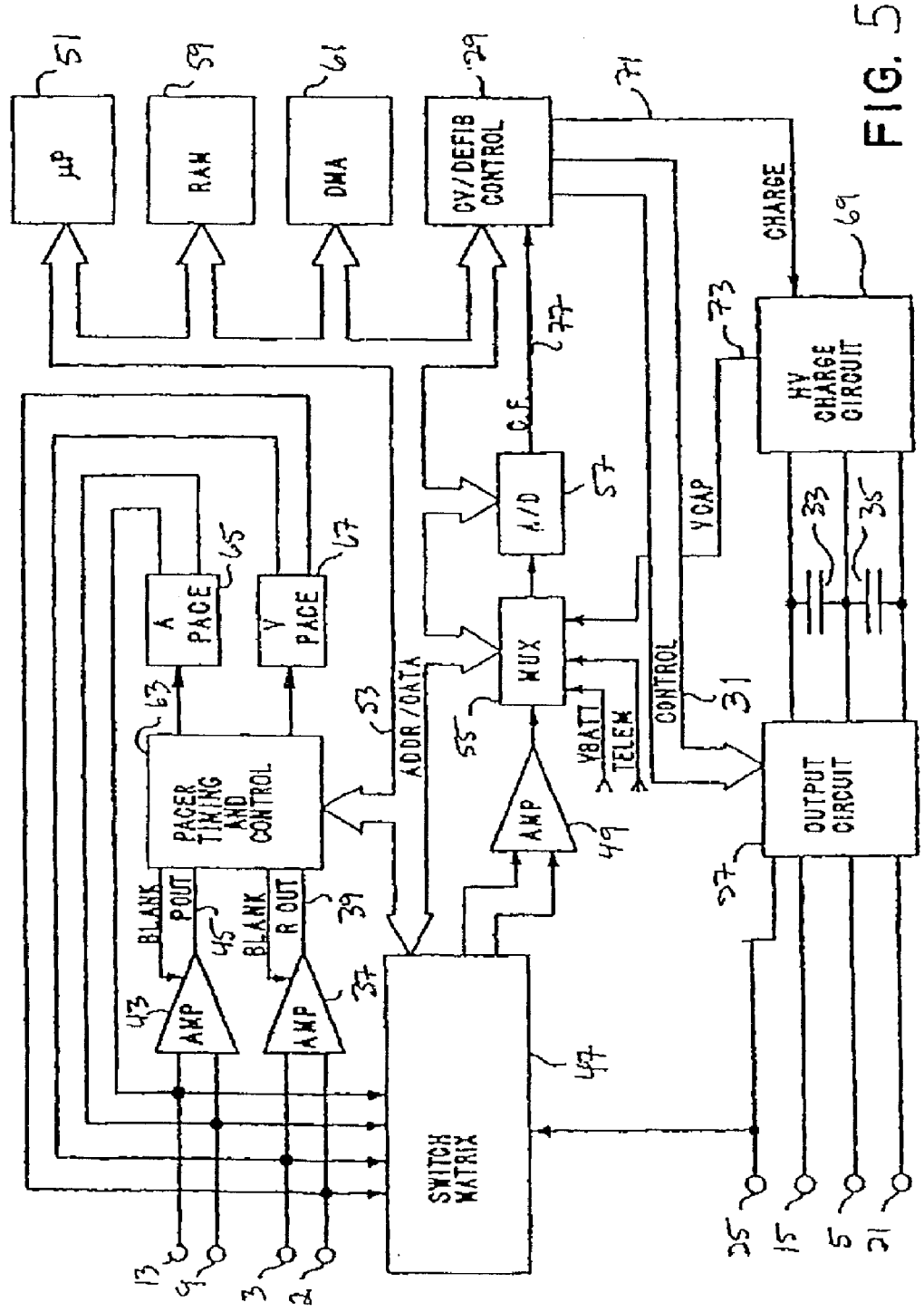
FIG. 5 is a functional block diagram of the IMD of FIG. 4.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

The implantable PCD is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al.

FIG. 5 is a functional schematic diagram of one embodiment of an implantable PCD of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

The PCD is provided with an electrode system. If the electrode configuration of FIG. 4 is employed, the electrode configuration correspondence may be as follows. Electrode 25 in FIG. 5 includes the uninsulated portion of the housing of the PCD. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, to Keimel et al.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selection may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known in the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known in the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann et al., U.S. Pat. No. 4,880,005 issued to Pless et al. and U.S. Pat. No. 4,830,006 issued to Haluska et al. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170. Atrial fibrillation detection methodologies are disclosed in Published PCT Application Ser. No. U.S.92/02829, Publication No. WO92/18198, by Adams et al., and in the article "Automatic Tachycardia Recognition", by Arzbaecher et al., published in PACE, May–June, 1984, pp. 541–547.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al. and U.S. Pat. No. 4,587,970, issued to Holley et al., may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and, in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al. However, any known cardioversion or defibrillation pulse control circuitry is believed to be usable in conjunction with various embodiments of the present invention. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. Examples of output circuitry for delivery of biphasic pulse regimens to multiple electrode systems may be found in U.S. Pat. No. 4,953,551 to Mehra et al. and in U.S. Pat. No. 4,727,877 to Kallock.

An example of circuitry which may be used to control delivery of monophasic pulses is disclosed in U.S. Pat. No. 5,163,427 to Keimel. Output control circuitry similar to that disclosed in the above cited patent issued to Mehra et al. or U.S. Pat. No. 4,800,883 to Winstrom, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennett et al. The present invention is believed to find wide application to various implantable electrical devices.

An example of circuitry which may be used to control delivery of monophasic pulses is disclosed in U.S. Pat. No. 5,163,427 to Keimel. Output control circuitry similar to that disclosed in the above-cited patent issued to Mehra et al. or U.S. Pat. No. 4,800,883 to Winstrom, may also be used in conjunction with various embodiments of the present invention to deliver biphasic pulses.

Figure 6:
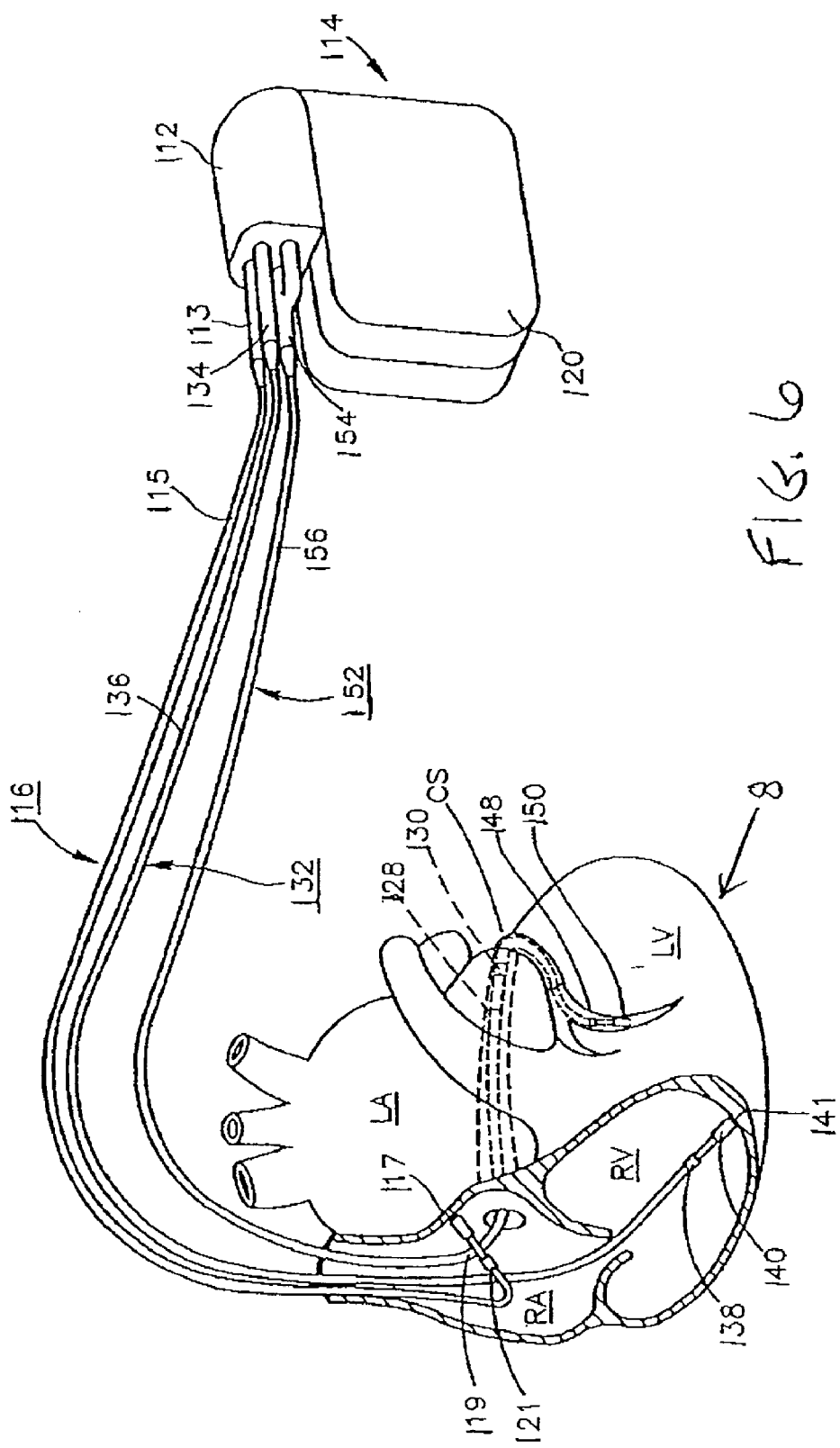
FIG. 6 is an IMD illustrating a multiple channel bi-atrial and/or bi-ventricular pacing system coupled with a patient's heart in accordance with another embodiment of the present invention.

FIG. 6 is a schematic representation of an (IMD) 114 that includes a four-channel cardiac pacemaker such as that described in U.S. Pat. No. 6,070,101 to Struble et al. The inline connector 113 of a right atrial lead 116 is fitted into a bipolar bore of IMD connector block 112 and is coupled to a pair of electrically insulated conductors within lead body 115 that are connected with distal tip right atrial pace-sense electrode 119 and proximal ring right atrial pace-sense electrode 121. The distal end of the right atrial lead 116 is attached to the right atrial wall by a conventional attachment mechanism 117. Bipolar endocardial right ventricle lead 132 is passed through the vein into the right atrial chamber of the heart 8 and into the right ventricle where its distal ring and tip right ventricular pace-sense electrodes 138 and 140 are fixed in place in the apex by a conventional and distal attachment mechanism 141.

The right ventricular lead 132 is formed with an inline connector 134 fitting into a bipolar bore of IMD connector block 112 that is coupled to a pair of electrically insulated conductors within lead body 136 and then connected with distal tip right ventricular pace-sense electrode 140 and proximal ring right ventricular pace-sense electrode 138.

In this particular illustrative embodiment, although other types of leads may be used, a quadripolar, endocardial left ventricular coronary sinus (CS) lead 152 is passed through a vein into the right atrial chamber of the heart 8, into the CS, and then inferiorly in the great vein to extend to the distal pair of left ventricular CS pace-sense electrodes 148 and 150 alongside the left ventricular chamber and leave the proximal pair of left atrial CS pace-sense electrodes 128 and 130 adjacent the left atrial chamber. The left ventricular CS lead 152 is formed with a four-conductor lead body 156 coupled at the proximal end to a bifurcated inline connector 154 fitting into a pair of bipolar bores of IMD connector block 112. The four electrically insulated lead conductors in left ventricular CS lead body 156 are separately connected with one of the distal pair of left ventricular CS pace-sense electrodes 148 and 150 and the proximal pair of left atrial CS pace-sense electrodes 128 and 130.

The IMD 114 may comprise, for example, similar circuitry and connections as shown in FIG. 3 for each of the multiple leads to establish the multiple pacing/sensing channels provided for each respective pair of pace-sense electrodes associated with each chamber of the heart as shown in FIG. 6. For the sake of convenience, such circuitry is not described further. For example, channel circuitry for pacing/sensing the left atrial chamber is associated with pace-sense electrodes 128 and 130 adjacent the left atrium. One skilled in the art will recognize that each sensing/pacing channel may include a sense amplifier and pace output pulse generator coupled through the respective pacing/sensing lead.

Although the pacing system shown in FIG. 6, shall not be described in detail for simplicity purposes, it will be recognized that multiple chambers may be paced/sensed via respective channels for such chambers. As such, for example, bi-atrial and/or bi-ventricular pacing may be performed as would be readily apparent to one skilled in the art.

With various embodiments of medical devices, e.g., implantable medical devices, described above, it will become apparent from the description below that the present invention may be applied to any multi-chamber cardiac pacing system, e.g., dual chamber, triple chamber, and quadruple chamber pacing systems. For example, the present invention may be applied to a three-chamber atrial-bi-ventricular pacing apparatus, a dual chamber pacing apparatus, a dual chamber defibrillator, etc. In other words, for example, the present invention may be applied to any implantable medical device that employs multi-site pacing. For example, some devices that may be modified to include the pacing techniques according to the present invention may include: InSync-ICD (e.g., Medtronic InSync ICD (Model 7272)); InSync III three chamber atrial-bi-ventricular pacers; and all VDD(R)/DDD(R) pacemakers including dual chamber right atrial/left ventricular pacers. Other modifiable devices may include: the Medtronic Marquis DR DDDR-ICD; other dual chamber right atrial/left ventricular defibrillators; Marquis AT right-left atrial/ventricular defibrillators; and Marquis InSync atrial/biventricular defibrillators.

Figure 7:
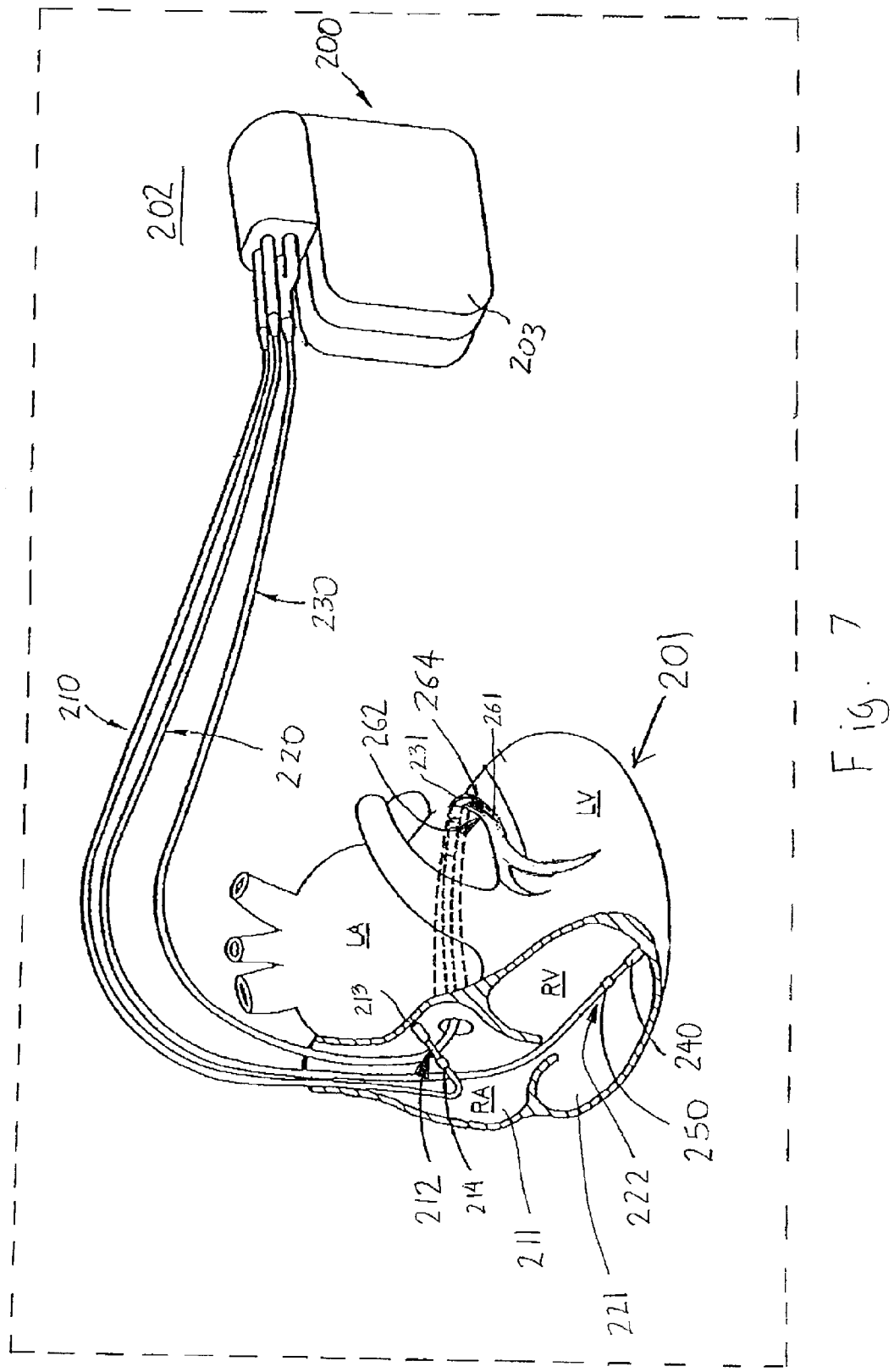
FIG. 7 is an IMD illustrating a multiple channel bi-atrial and/or bi-ventricular pacing system coupled with a patient's heart in accordance with another embodiment of the present invention.

FIG. 7 illustrates an IMD, e.g., a pacemaker or pacemaker-cardioverter-defibrillator as generally illustrated by reference numeral 200, as it may be implanted within human or mammalian body 202. Leads 210, 220, and 230 extend from PCD 200 into various chambers of heart 201. More particularly, lead 210 extends into right atrium 211; lead 220 extends into right ventricle 221; and lead 230 extends through the coronary sinus to left lateral coronary vein 231.

Leads 210, 220, and 230 may include unipolar or bipolar electrodes at their respective distal ends as is known in the art. For illustrative purposes, leads 210, 220, and 230 are each shown with bipolar electrodes. That is, distal end of lead 210 includes electrode assembly 212 having tip (e.g., cathode) electrode 213 and ring (e.g., anode) electrode 214. Distal end of lead 220 may similarly include electrode assembly 222 having tip (e.g., cathode) electrode 240 and ring (e.g., anode) electrode 250. Finally, distal end of lead 230 may include electrode assembly 262 having tip (e.g., cathode) electrode 261 and ring (e.g., anode) electrode 264. Other leads and electrodes located in heart 201 or elsewhere in body 202 may also be included without departing from the scope of the invention.

Preferably, capture detection is done immediately following delivery of a pacing pulse. In many conventional PCDs, capture detection is accomplished with the same electrodes that deliver the pacing pulse. However, as discussed above, such capture detection may be disrupted by the presence of polarization potentials. The polarization potential is normally caused by the capacitance of the electrode-tissue interface after delivery of the pacing pulse. This polarization potential may significantly impede the detection of the evoked response signal necessary for effective capture detection.

To minimize or avoid the effects of polarization potential during capture detection, devices and methods of the present invention permit interrogation of numerous electrode pairs and selection of the electrode pair having the lowest detected polarization potential for each paced chamber. This selected electrode pair may then be programmed for use in subsequent capture detection of the chamber. By selecting a combination of electrodes for sensing the evoked response signal that is different from the combination of electrodes used for pacing, the effect of the polarization potential on evoked response detection is reduced.

FIG. 7 illustrates an exemplary configuration for multi-chamber pacing that may utilize the concepts of the present invention. Signals or cardiac "vectors" representing polarization potential may be measured between the various combinations of electrodes after delivery of calibrating pacing pulses. Once the vector having the lowest polarization potential magnitude is identified, that vector may be programmed for use in detecting subsequent capture of the selected chamber.

Additional information on vectorcardiography may be found in pending U.S. patent application Ser. No. 10/003, 547, filed Oct. 31, 2001, and entitled "METHOD AND APPARATUS FOR DEVELOPING A VECTORCARDIO-GRAPH IN AN IMPLANTABLE MEDICAL DEVICE, as well as generally in other patent documents (see e.g., U.S. Pat. No. 4,569,357 to Sanz et al.; U.S. Pat. No. 4,136,690 to Anderson et al.; U.S. Pat. No. 5,458,116 to Egler; U.S. Pat. No. 6,052,615 to Field et al.; U.S. Pat. No. 4,478,223 to Allor; and U.S. Pat. No. 5,740,811 to Hedberg et al.).

Assuming electrode assemblies 212, 222, and 262 of FIG. 7 are each bipolar (e.g., all include a cathodic tip and an anodic ring), nine different combinations or pairs of sensing electrodes can be measured as shown in Table II.

TABLE II

| Electrode Combinations (Vectors) |
| --- |
| Right Ventricle (RV) cathode (240) to Left Lateral Coronary Vein (LV) cathode (261) |
| RV anode (250) to LV cathode (261) |
| RV cathode (240) to LV anode (264) |
| RV anode (250) to LV anode (264) |
| RV anode (250) and cathode (240) to LV cathode (261) |
| RV anode (250) and cathode (240) to LV anode (264) |
| RV cathode (240) to LV anode (264) and cathode (261) |
| RV anode (250) to LV anode (264) and cathode (261) |
| RV anode (250) and cathode (240) to LV anode (264) and cathode (261) |

Each vector, or electrode combination, may yield a different polarization potential after delivery of the pulsing pace.

Figure 8:
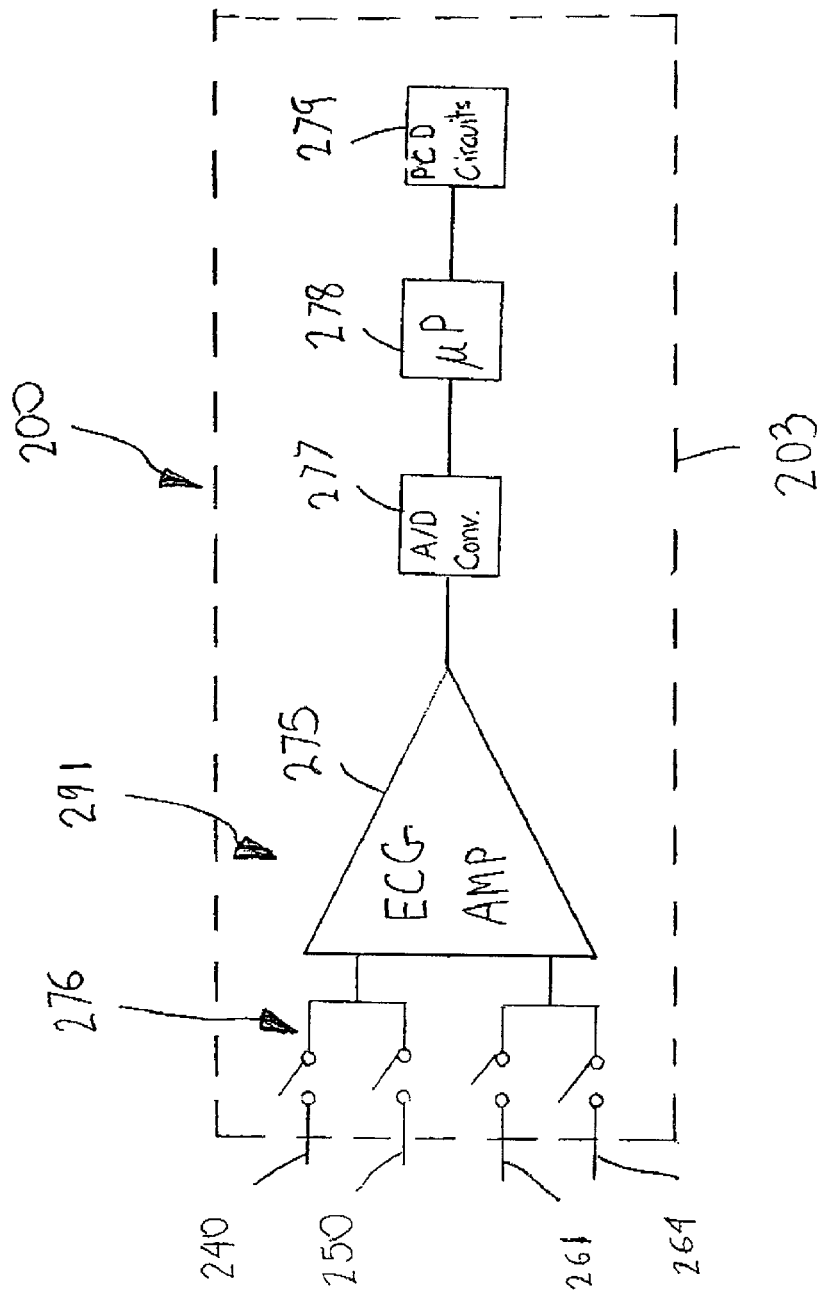
FIG. 8 is a vector recording circuit in accordance with one embodiment of the invention.

FIG. 8 illustrates vector recording circuit 291 used to implement the exemplary embodiment of the invention shown in FIG. 7. The circuit 291 is preferably located within casing or housing 203 (see FIG. 7) of PCD 200. For simplicity, the remaining circuits of PCD 200 are not illustrated in this view.

To determine the vector having the lowest polarization potential, switch array 276 is provided. Switch array 276 may be controlled via external programming apparatus, as is known in the art, to select most any combination of electrodes to yield most any available vector. Signals between electrode combinations may be recorded with ECG amplifier 275 which is, in turn, coupled to A/D converter 277, microprocessor 278, and remaining PCD circuits as represented by 279.

Combinations of electrodes analogous to those illustrated in Table II. exist for recording vectors between the right atrial electrodes 213, 214 and the left lateral coronary vein electrodes 261, 264. Moreover, while not specifically identified, other electrodes may couple to switch array 276. For example, housing 203 of PCD 200, various atrial electrodes (see e.g., right atrial electrodes 119 and 121 and left atrial electrodes 128 and 130 of FIG. 6), and other electrodes located elsewhere within or on the body may be combined with any other electrode to establish a vector as described herein. Thus, the electrode combinations described above are exemplary only and other embodiments utilizing most any electrodes selected from a plurality of electrodes are certainly possible.

Figure 9:
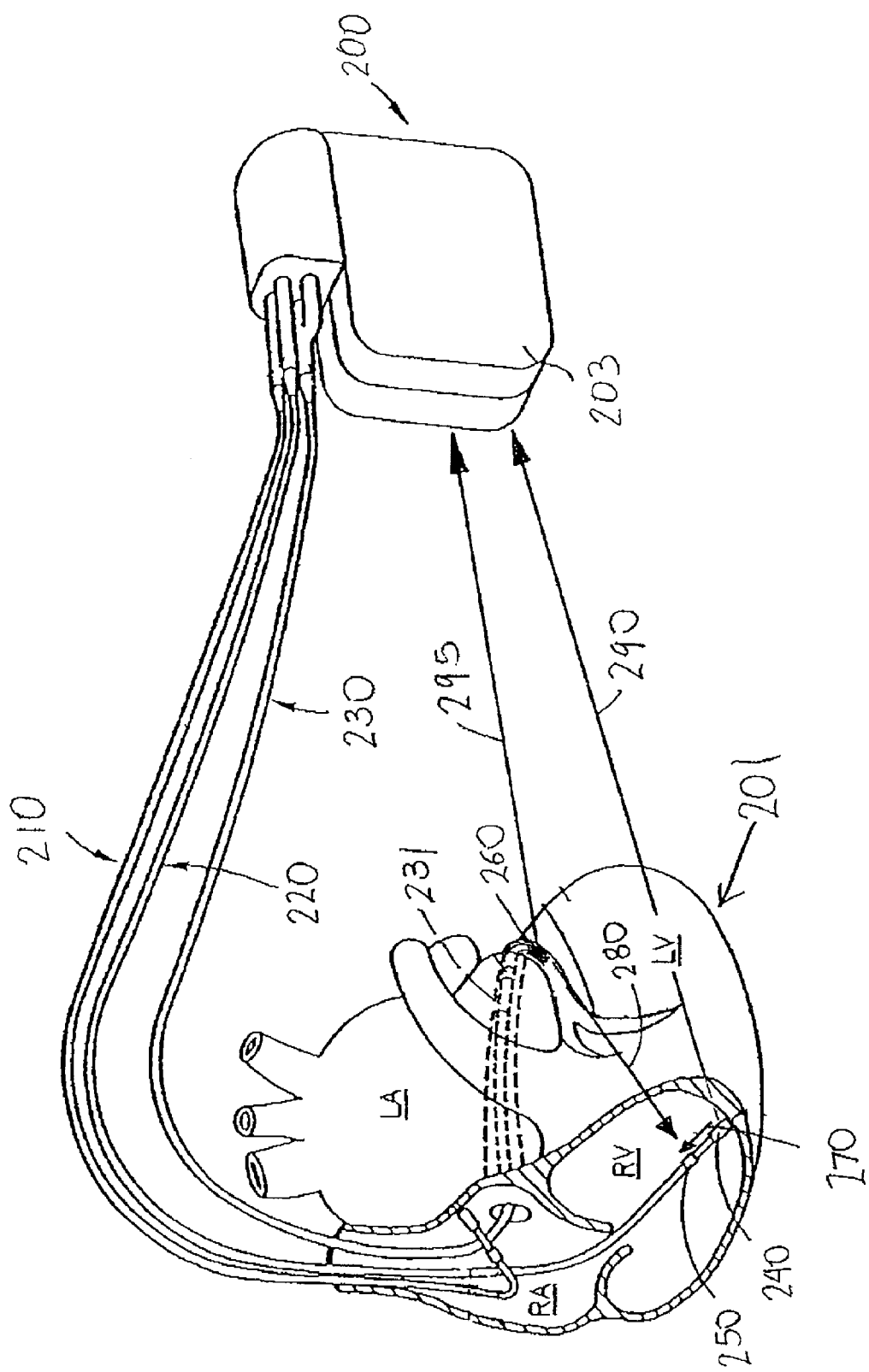
FIG. 9 is an IMD illustrating exemplary pacing vectors for a multiple channel bi-atrial and/or bi-ventricular pacing system in accordance with one embodiment of the present invention.

In one example, a three-chamber cardiac resynchronization pacing system including PCD 200 as illustrated in FIG. 9 is provided. The pacing system includes atrial lead 210 implanted within the right atrial appendage, right ventricular lead 220 implanted into the right ventricular apex, and left ventricular lead 230 implanted in the left lateral coronary vein. Right ventricular lead 220 preferably includes cathode electrode 240 at its tip and anode ring electrode 250 located proximate electrode 240 as is known in the art. In this embodiment, left ventricular lead 230 includes unipolar active electrode 260 at its tip.

For delivery of right ventricle pacing pulses, three pacing vectors may be selected: vector 270 for delivering a pacing pulse between electrodes 250 and 240 of lead 220; vector 280 for delivering a pacing pulse between electrode 250 and electrode 260; and vector 290 for delivering a pacing pulse between casing 203 of PCD 200 and electrode 240, with the vectors 270 and 290 being preferred.

Left ventricular pacing is preferably done using electrodes 260 and casing 203, e.g., using pacing vector 295. If lead 230 incorporates a bipolar electrode, (see e.g., FIG. 7), more sophisticated pacing vector combinations are possible as would be readily discernable.

Figure 10:
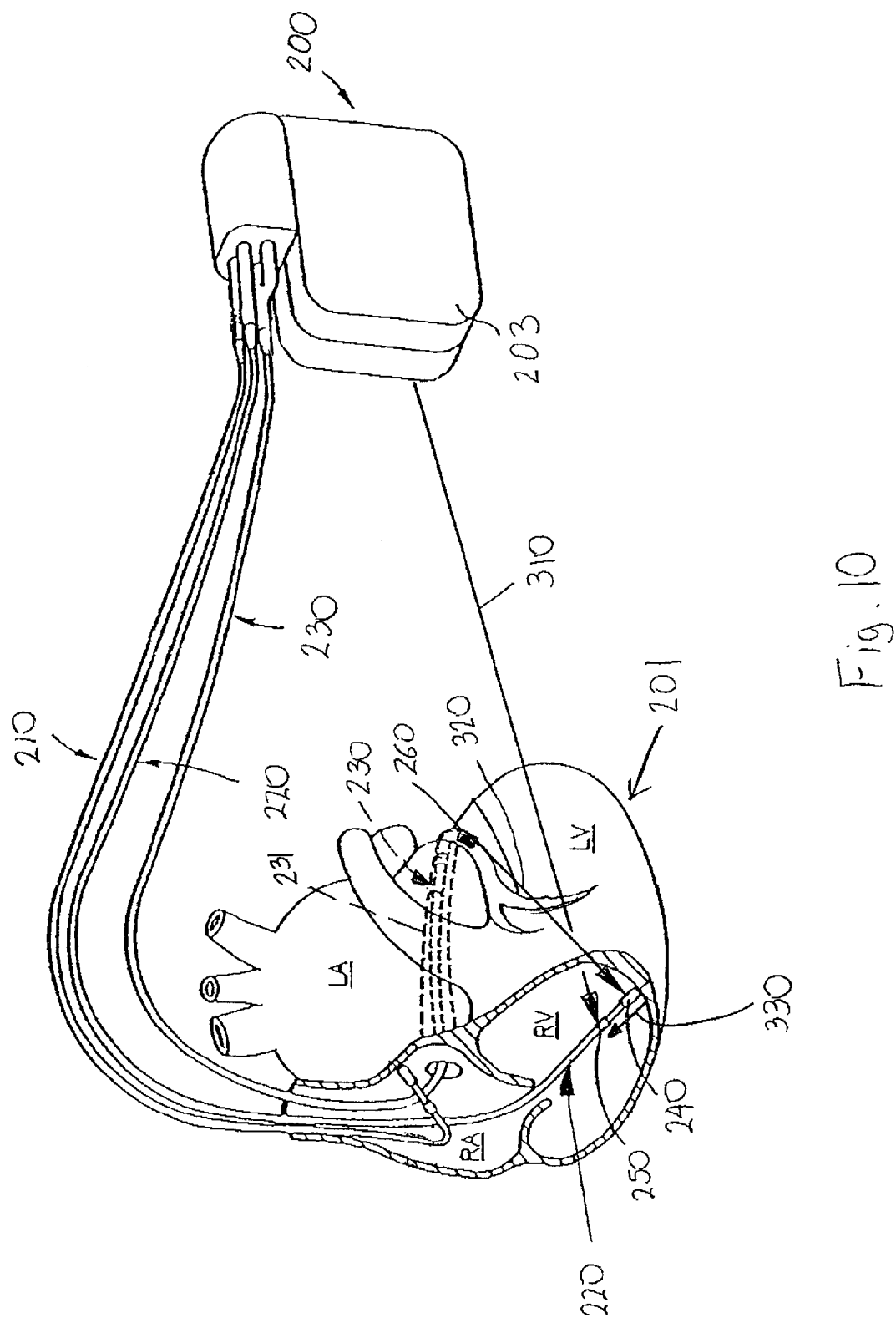
FIG. 10 illustrates exemplary ventricular sensing vectors for use with the IMD of FIG. 9.

FIG. 10 illustrates potential ventricular sensing vectors that may be used with PCD 200 of FIG. 9 to detect evoked response signals after delivery of an electrical stimulus, e.g., a pacing pulse. In this view, vector 310 may be measured between casing 203 of PCD 200 and electrode 250; vector 320 may be measured between electrodes 240 and 260; and vector 330 may be measured between electrodes 240 and 250.

Accordingly, pacing pulses may be delivered via any of a multitude of electrodes while capture may be detected using the same or, more preferably, a different combination of electrodes. That is, it is not necessary that the same vector be used for both pacing pulse delivery and evoked response sensing. Rather, the vector used for evoked response detection (i.e., capture detection) should be the vector determined to yield the lowest polarization potential as described herein, particularly, with reference to FIG. 11.

Figure 11:
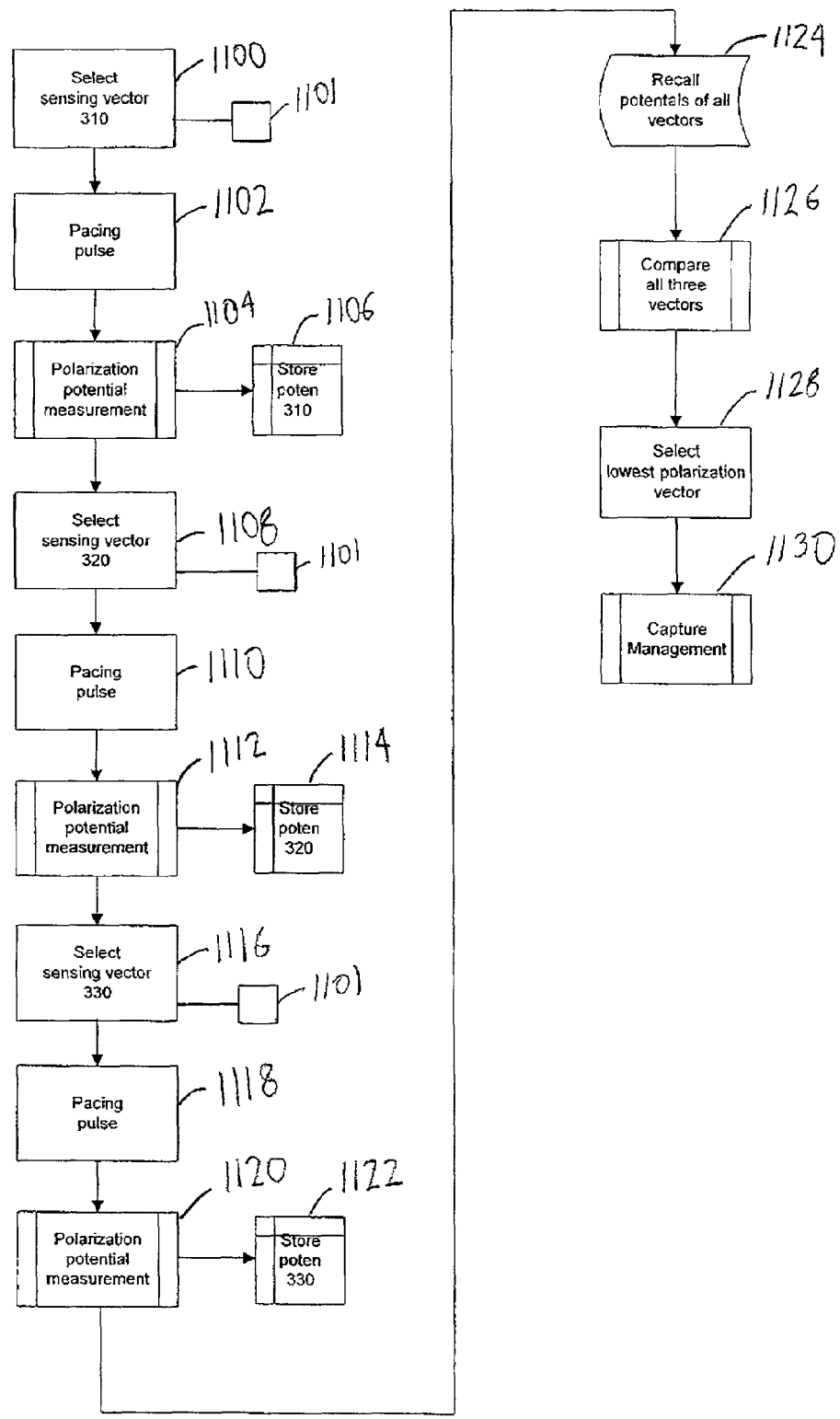
FIG. 11 is a flow chart illustrating a method for determining a sensing vector having the lowest polarization potential in accordance with one embodiment of the invention.

FIG. 11 is a flow chart illustrating an exemplary algorithm for selecting a pair of electrodes exhibiting the lowest polarization potential after a particular electrical stimulus, e.g., a calibrating pacing pulse, is provided, corresponding to a particular chamber of the heart for which capture detection may be performed. In describing this Figure, reference is made to PCD 200 of FIG. 10 and circuit 291 of FIG. 8.

Once PCD 200 is implanted, programming apparatus 1101 may be used to telemeter programming parameters to, and record diagnostic information from, PCD 200. In particular, programming apparatus 1101 is preferably capable of controlling switch array 276 (see FIG. 8) to select the various combinations of electrodes that establish the desired sensing vectors.

For example, electrode 250 and casing 203 may be connected to the sensing amplifier, e.g., via switch array 276, at 1100 to yield sensing vector 310. After delivery of a pacing pulse to the subject chamber at 1102, polarization potential is measured at 1104 and its value stored at 1106. Electrodes 240 and 260 may then be connected to the sensing amplifier at 1108 to yield sensing vector 320. After delivery of a pacing pulse at 1110, polarization potential is measured at 1112 and its value stored at 1114. Switch array 276 may then be configured to connect electrodes 240 and 250 to sensing amplifier 275, yielding sensing vector 330 at 1116. After delivery of a pacing pulse at 1118, polarization potential is measured at 1120 and its value stored at 1122.

This process of selecting a sensing vector, providing a pacing pulse, measuring the polarization potential, and storing the polarization potential may be repeated until all desired electrode combinations are exhausted. Once the polarization potential of all or some electrode combinations are stored, the values may be recalled at 1124 and compared at 1126. The vector having the lowest value is selected at 1128 and is programmed for use in subsequent capture management at 1130. Various embodiments that use this vector during capture detection are described elsewhere herein.

The procedure illustrated in FIG. 11 may be repeated for each paced chamber. e.g., each ventricle and/or atrium for which capture detection is desired.

Figure 12:
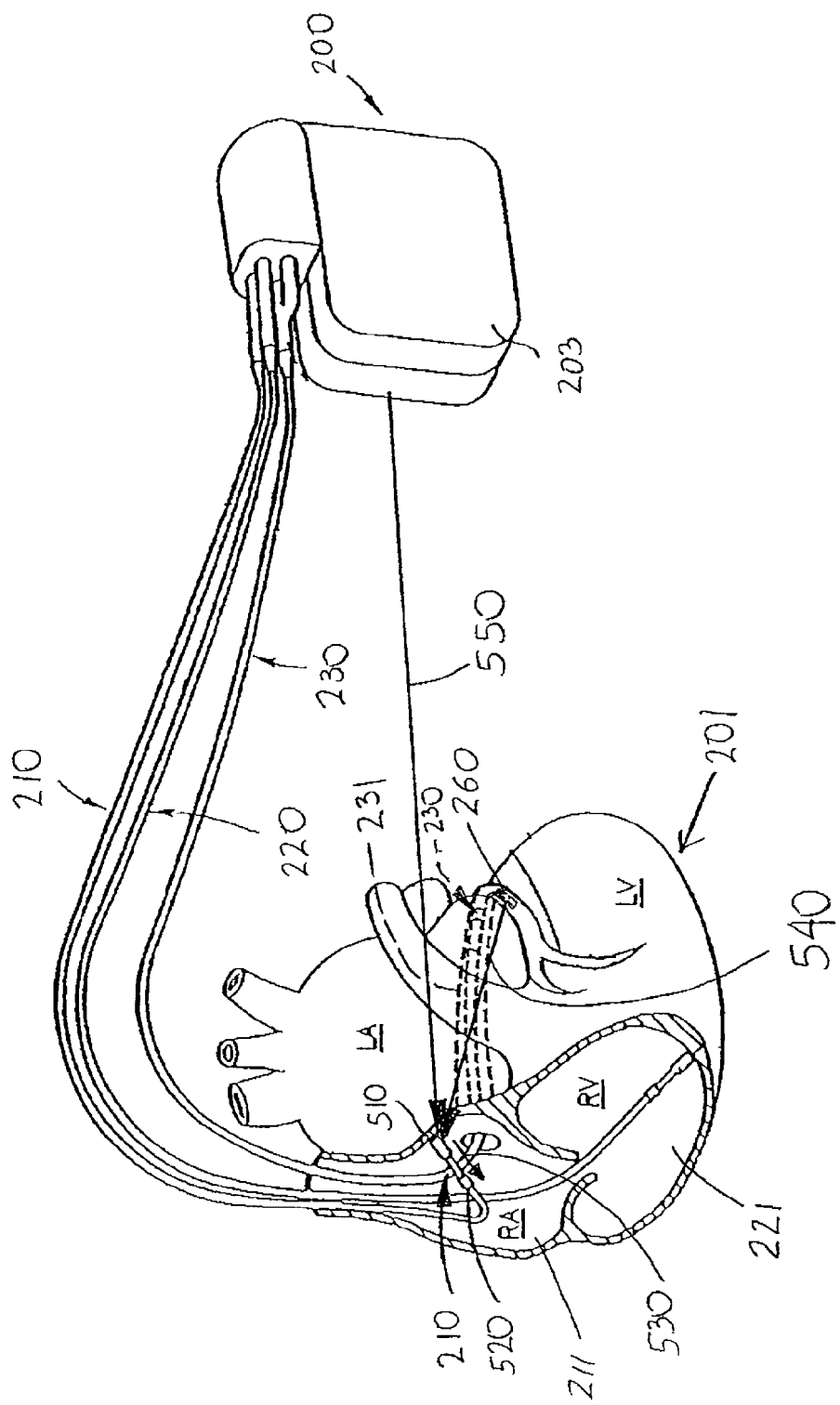
FIG. 12 is an IMD illustrating a multiple channel bi-atrial and/or bi-ventricular pacing system, illustrating exemplary atrial sensing vectors.

Having described vectors for use with bi-ventricular pacing, FIG. 12 illustrates in more detail a three-chamber PCD system incorporating atrial pace sensing for use with resynchronization bi-ventricular pacing systems. Like the embodiments already described, FIG. 12 illustrates a pacing system having atrial lead 210 implanted proximate right atrium 211, e.g., within the right atrial appendage, right ventricular lead 220 implanted proximate apex of right ventricle 221, and left ventricular lead 230 implanted in left lateral coronary vein 231 proximate the left ventricle.

Atrial lead 210 includes cathode electrode 510 at its tip and anode ring electrode 520 proximate the tip. As already described above, left ventricular lead 230 includes unipolar electrode 260 at its tip. Right ventricular lead 220 is also included but its electrodes are not utilized for atrial pacing/sensing in this particular embodiment and are thus not further described herein.

At least two atrial pacing vectors are: vector 530 for a pacing pulse delivered between two electrodes 510 and 520 of atrial lead 210; and vector 550 for a pacing pulse delivered between electrode 510 and casing 203 of PCD 200.

In addition to these pacing vectors, at least three atrial sensing vectors are possible: vector 530 when electrodes 510 and 520 of lead 210 are connected to atrial sensing amplifier (see amp 291 of FIG. 8 or amp 660 of FIG. 13); vector 550 when electrode 510 and casing 203 of PCD 200 are connected to the atrial sensing amplifier; and vector 540 when electrode 510 of lead 210 and electrode 260 of lead 230 are connected to the atrial sensing amplifier.

While not illustrated, another atrial sensing vector may be defined when the vector between atrial electrode 520 of lead 210 and electrode 260 of lead 230 are connected to the atrial sensing amplifier.

The latter two vectors (i.e., the vector 540 between electrodes 510 and 260, and the vector formed between electrodes 520 and 260) may provide a better representation of left atrial evoked potential than the other vectors. Moreover, these two vectors may yield a signal that more accurately represents depolarization of not one but both atria. As a result, these vectors may be particularly advantageous for sensing atrial evoked potential (e.g., atrial capture detection) in resynchronization devices such as atrio bi-ventricular pacemakers.

Moreover, the projection of vector 530 onto vector 540 is minimal, indicating that the stimulus artifact, as well as the polarization potential caused by the pacing pulse, delivered between electrodes 510 and 520 has a relatively low amplitude.

Figure 13:
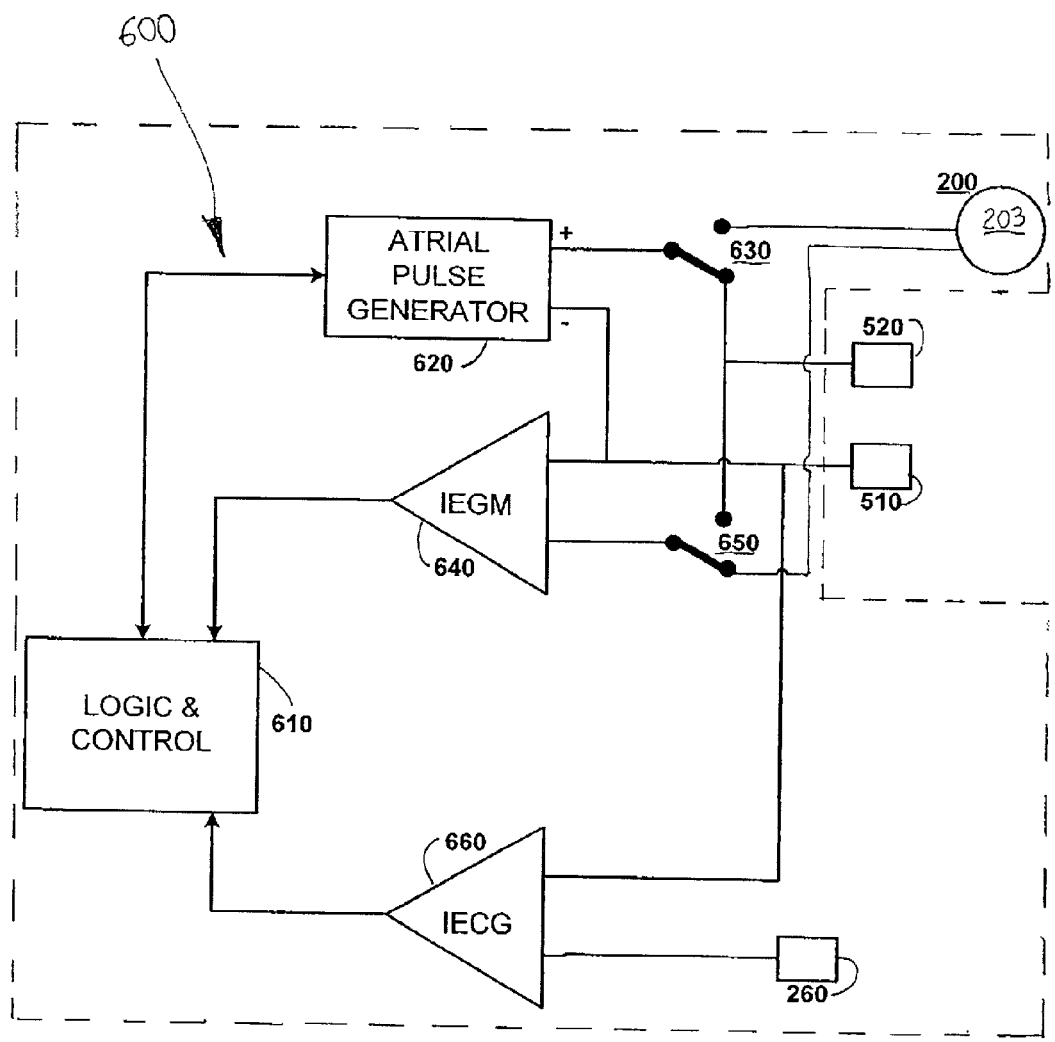
FIG. 13 illustrates an exemplary atrial output circuit for use with IMDs of the present invention.

Atrial output circuit 600 of PCD 200 may be configured as illustrated in the block diagram of FIG. 13. Only those elements of the output circuit 600 necessary to an understanding of the invention are illustrated in FIG. 13. Those of skill in the art will realize that other circuits/features as known in the art may also be included.

Logic and control circuitry 610 generally controls the functionality of the circuit 600. Programmable pulse generator 620 produces pacing pulses of adjustable amplitude and pulse duration based on sensed and programmed parameters. Switch 630 can select either unipolar or bipolar stimulation, e.g., the positive pole of pulse generator 620 may be connected to electrode 520 or to the casing 203, respectively (see FIG. 12). The negative pole of pulse generator 620 is preferably coupled to electrode 510 (see FIG. 12).

Sensing filter-amplifier 640 has gain and bandwidth adjustment which are preferably optimized for intracardiac atrial electrogram (IEGM) sensing used for pacing timing cycles as known in atrial sensing cardiac pacemakers. Switch 650 can be programmed to select either unipolar or bipolar sensing, e.g., sensing amplifier 640 may be connected to electrodes 510 and 520 or to electrodes 510 and casing 203 (see FIG. 12).

Filter-amplifier 660 has gain and bandwidth adjustment which are preferably optimized for intracardiac electrocardiogram (IECG) recording between electrodes 260 and 510 (see FIG. 12). As described above, sensing between electrodes 260 and 510 yields the lowest atrial polarization potential following an atrial pacing pulse and thus is appropriate for use in atrial capture detection.

Once again, IECG recording could also be done between electrodes 260 and 520 (see FIG. 12). However, the vector measured between electrodes 260 and 520 is believed to be of negligible difference as compared to the vector between electrodes 260 and 510.

Signals provided by amplifier 660 to logic and control circuitry 610 are used for atrial evoked potential detection due to the fact that they have the best ratio between evoked potential and polarization potential following an atrial pacing pulse. As known in physiology, the atrial depolarization wave starts in the right atrium and spreads towards the left atrium. The vector 530 (see FIG. 12) yields only information about right atrial depolarization while the vector 540 yields information about both right and left atrial depolarization. That is, signals recorded via vector 540 include projections of multiple atrial depolarization vectors. As a result, vector 540 yields particularly advantageous information about atrial depolarization wave spread. Such information may be used to detect capture and control pacing as desired.

Another aspect of the present invention is directed to a problem particular to bi-ventricular pacing, both with and without atrial pacing. Unlike single ventricular pacing, loss of capture in one chamber in bi-ventricular systems does not result in loss of evoked QRS complex as the other ventricle may still pace. However, the morphology or form of the QRS wave typically will change, e.g., will become wider, when one of the two ventricles is not captured. As a result, resynchronization therapy in bi-ventricular pacing should produce a normal, e.g., narrow, QRS complex. That is, achieving (and successfully detecting) normal QRS complex width (duration) is one goal of bi-ventricular capture management.

Figure 14:
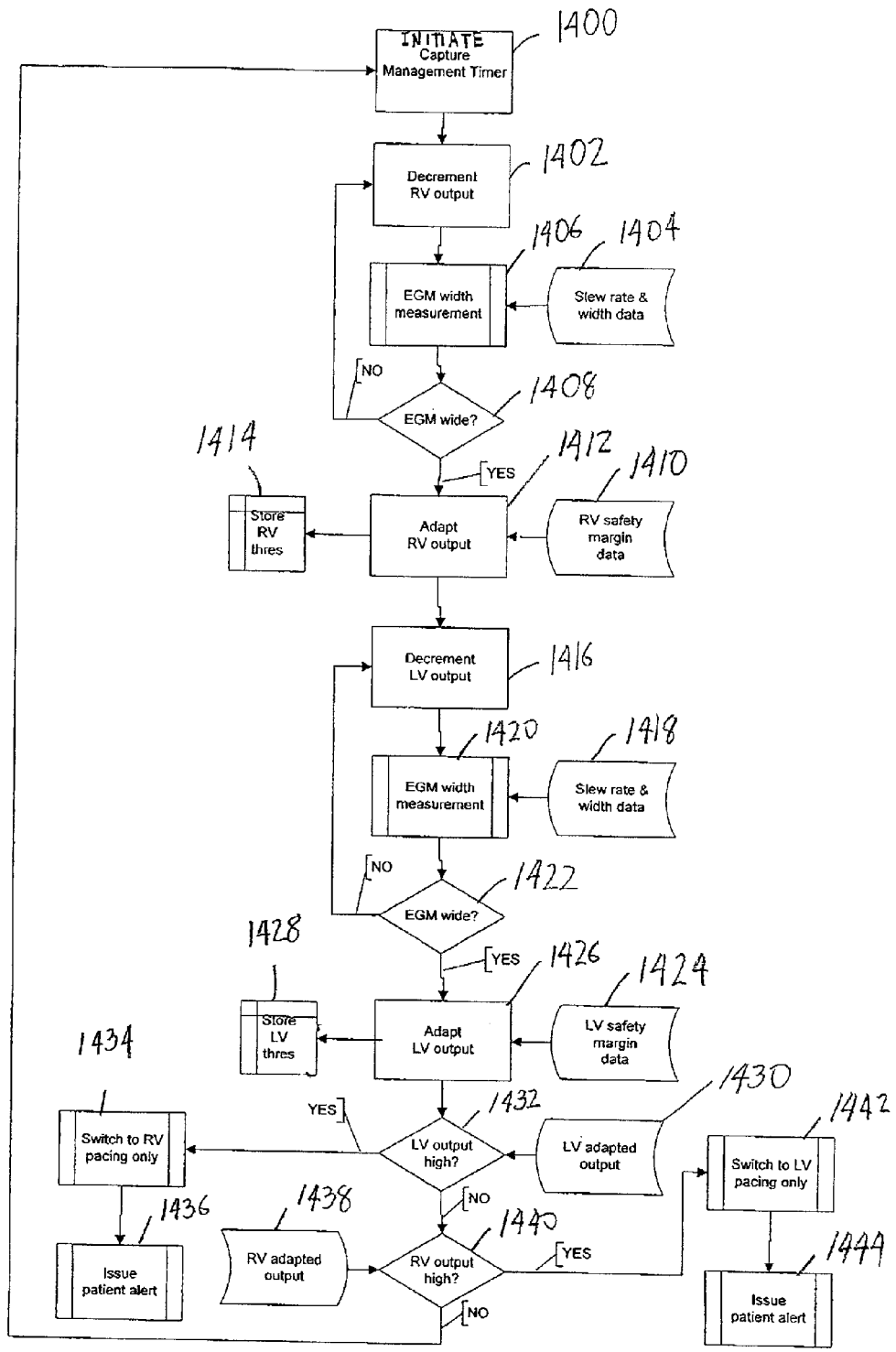
FIG. 14 is a flow chart illustrating a method of threshold determination and single ventricular loss of capture in multi-chamber pacing for use with IMDs of the present invention.

FIG. 14 illustrates a flow chart of an exemplary ventricular capture management process for bi-ventricular pacing in accordance with the present invention. Programmable capture management timer initiates a desired capture management algorithm at 1400 upon the prescribed time interval (e.g., once a day at specific time, every hour, once a month, etc.). Upon initiation, a right ventricular threshold is measured by successive decrementing of right ventricular output at 1402 while left ventricular output is maintained at a fixed, normal level. Such decrementing will not result in complete ventricular loss of capture but rather may only result in local loss of right ventricular capture. Therefore, EGM width, i.e., the width of the QRS complex, may be measured by any method known in the art at 1406. Preferably, EGM width is sensed using the electrode combination having the lowest polarization potential for the right ventricle as already determined, for example, by the method illustrated in FIG. 11.

In some embodiments, EGM width measurement may be accomplished utilizing predetermined slew-rate and width data stored in memory at 1404. If EGM width is determined to be within normal preprogrammed parameters, e.g., the QRS complex is "narrow," at 1408 control returns to 1402 where the right ventricular output is decremented again and loop 1402–1408 continues until EGM width is detected to be abnormal, e.g., until the width of the QRS complex is determined to be "wide," at 1408. The point at which the right ventricular output first produces a wide EGM width measurement indicates that right ventricular output is just below the right ventricular threshold.

Once EGM width is determined to be wide, the prescribed previously programmed right ventricular threshold margin data stored at 1410 is used to adapt a magnitude of the right ventricular output at 1412 such that capture will be maintained. The right ventricular threshold may be stored into memory at 1414 for future interrogation and for formation of a right ventricular threshold trend curve, the latter being known in the art.

Left ventricular threshold is measured in a similar manner beginning with successive decrementing of left ventricular output at 1416 while right ventricular output is maintained at the prescribed magnitude. Once again, local loss of capture of the left ventricle will not cause total ventricular loss, e.g., QRS complex will still be detectable upon loss of capture of the left ventricle. Thus, EGM width measurement is done at 1420 utilizing predetermined slew-rate and width data stored at 1418. Once again, EGM width is preferably sensed using the electrode combination having the lowest polarization potential in the left ventricle as determined herein by, for example, the method illustrated in FIG. 11. If EGM width is determined at 1422 to be narrow, left ventricular output is decremented further and the loop 1416–1422 continues until the measured EGM width becomes wide at 1422.

As with right ventricular threshold detection, EGM width will be determined to be wide at 1422 when the left ventricular output value is just below a left ventricular capture threshold. The left ventricular output magnitude is therefore adapted at 1426 utilizing left ventricular safety margin data stored at 1424 such that capture will be maintained. Further, the left ventricular threshold value may be stored into memory at 1428 for future interrogation and formation of a left ventricular threshold trend curve.

The method illustrated in FIG. 14 may also account for extreme changes in right and left ventricular thresholds which are sometimes attributable to excessive fibrous tissue overgrowth at the site of the pacing electrode(s). This threshold rise may result in what is sometimes referred to in the art as "exit block." To monitor threshold rise, devices and methods of the present invention may include algorithms to monitor the left and right ventricular outputs (according to their respective safety margins) and determine whether they are beyond a preprogrammed, acceptable level.

For example, left ventricular adapted output may be determined at 1432 (based upon data stored at 1430) to be beyond a predetermined threshold level while right ventricular output is determined to be normal. In this instance, bi-ventricular pacing may be discontinued. That is, the algorithm may switch to only right ventricular pacing at 1434. Preferably, a patient alert may be issued at 1436 as it is known in the art so that the patient seeks immediate medical treatment.

Similarly, if right ventricular adapted output is determined to be too high (based upon data stored at 1438) at 1440 while left ventricular output is determined to be within normal parameters, bi-ventricular pacing may again be discontinued. That is, PCD algorithms may, in this case, switch to left ventricular pacing only at 1442 and issue a patient alert at 1444.

By checking for excessive adapted outputs, excessive battery drain may be avoided. Moreover, patient alerts, (e.g., audible alert) may ensure prompt medical attention to any pathological development that may have caused the threshold rise (such as fibrosis, myocardial infarction, lead failure, etc.).

Most any methodology used to conduct EGM width analysis for ventricular LOC in a bi-ventricular pacing system may be used without departing from the scope of the invention. One preferably technique, that may be used (or modified for use in) the present invention, however, is disclosed in U.S. Pat. No. 5,312,441 to Mader et al.

In addition to distinguishing left or right ventricular LOC in a bi-ventricular pacing device by EGM width detection, it is also contemplated that LOC may be detected by a technique of wavelet comparison. One technique that utilizes wavelet comparison, albeit for discrimination between ventricular and supraventricular arrhythmias, is described in detail in U.S. Pat. No. 5,447,519 to Peterson. Such a method may be adapted for use with single ventricular LOC in bi-ventricular pacing as described below.

Figure 15:
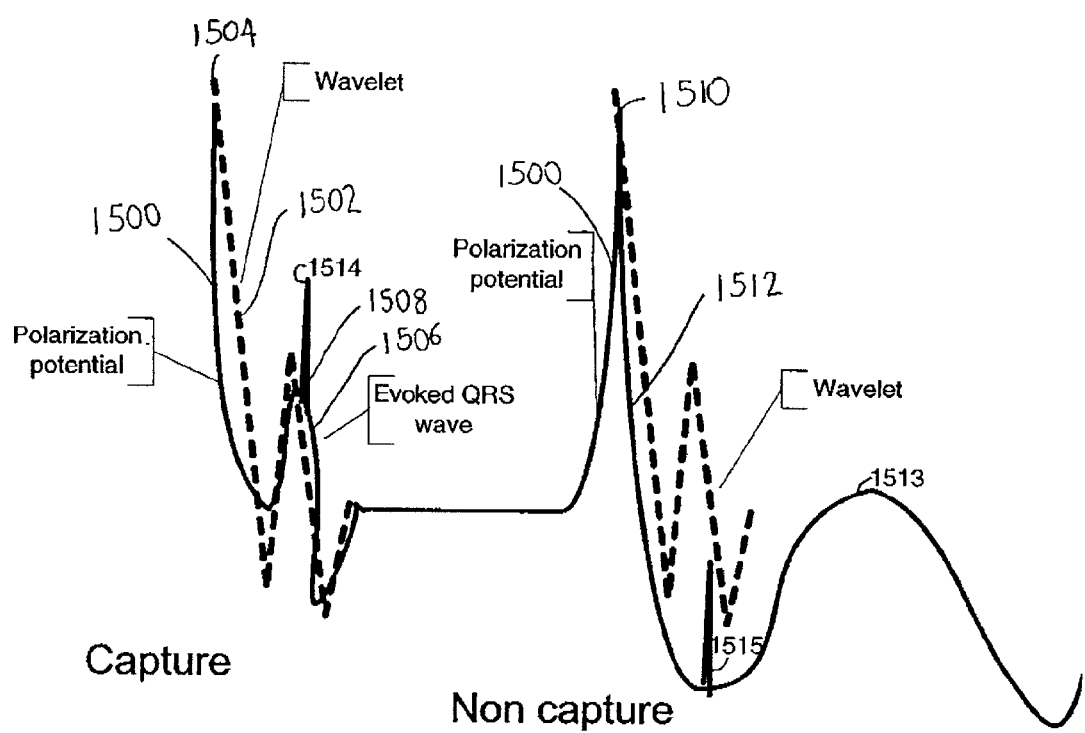
FIG. 15 is a diagrammatic illustration of a waveform analysis used to discriminate capture from loss of capture.

In FIG. 15, solid line 1500 represents a recorded intracardiac ECG waveform while dotted line 1502 represents a preprogrammed template or wavelet defining a normal QRS complex. Recorded intracardiac ECG waveform 1500 may be compared to wavelet 1502 to determine the degree of similarity between the two, e.g., to determine how much wavelet 1502 and ECG waveform 1500 agree in form and shape.

FIG. 15 illustrates ECG waveform 1500 beginning (from the left of the figure) with first pacing spike 1504 that decays exponentially. As first pacing spike 1504 decays, evoked potential 1506, e.g., an evoked QRS wave, which is superimposed over decaying first pacing spike 1504, is visible and has clearly recognized peak 1508. Thus, a high degree of matching between ECG waveform 1500 and wavelet 1502 after delivery of first pacing spike 1504 is indicated. Pacing spike 1514 represents the pacing spike delivered to the electrode(s) of the opposite ventricle.

FIG. 15 further illustrates decaying second pacing spike 1510. However, unlike first pacing spike 1504, second pacing spike 1510 has a magnitude below the capture threshold value. As a result, only the polarization potential is apparent after the second pacing spike 1510, e.g., an evoked potential is not clearly superimposed over exponentially falling polarization potential waveform 1512. Rather, a delayed or late evoked QRS wave 1513 occurs due to the prolonged interventricular conduction. That is, delayed QRS wave 1513 actually represents capture of pacing pulse 1515 delivered in the opposite ventricle. Thus, little or no matching of ECG waveform 1500 and wavelet 1502 occurs after second pacing spike 1510.

The high degree of matching between ECG waveform 1500 and wavelet 1502 after delivery of first pacing spike 1504 may indicate capture while the absence of similarity in waveform 1500 and wavelet 1502 after second pacing spike 1510 may indicate loss of capture. Thus, the type of signal processing illustrated in FIG. 15 and described above may yield recognition of an abnormal, e.g., wide, QRS complex.

Thus, devices and methods of the present invention provide numerous advantages over current multi-site pacing systems. For example, by utilizing different electrodes for capture than those used for pacing, the effects of polarization potential (resulting from delivery of a pacing pulse) on the detection of evoked response may be reduced, perhaps substantially. Moreover, numerous electrode combinations may be interrogated in multi-site pacing systems of the present invention to detect the electrode combination or vector that yields the lowest polarization potential following a pacing pulse. As a result, evoked response in a particular paced chamber may be better detected. In one embodiment, one or more electrode combinations or vectors may yield a signal that more accurately represents depolarization of both atria. Moreover, systems of the present invention may combine improved evoked response detection with QRS morphology analysis, e.g., EGM width criteria, to better detect loss of capture of a single ventricle of a bi-ventricular pacing system.

The complete disclosure of the patents, patent documents (including patent applications), and publications cited in the Background of the Invention, Detailed Description of the Preferred Embodiments, and elsewhere herein are incorporated by reference in their entirety as if each were individually incorporated.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to specific multi-chamber pacing systems, but rather may be used with most any pacemaker/cardioverter/defibrillator or other electrical stimulation device, implanted or external, that would benefit from the features described herein. The present invention further includes within its scope methods of making the devices described herein above.

What is claimed is:

1. A method for delivering therapy to a heart, comprising:
providing a plurality of electrodes in or around the heart;
delivering an electrical stimulus to the heart;
measuring a polarization potential vector between at least a first pair of electrodes of the plurality of electrodes and a second pair of electrodes of the plurality of electrodes;
comparing the polarization potential vector between at least the first pair of electrodes and the second pair of electrodes; and
selecting a sensing pair of electrodes from at least the first pair of electrodes and the second pair of electrodes that yields the lowest polarization potential vector, the sensing pair of electrodes operable for use in sensing an evoked response of the heart to a subsequent electric stimulus delivered thereto.

2. The method of claim 1, further comprising programming an implantable medical device to utilize the selected sensing pair of electrodes to sense the evoked response during capture management.

3. The method of claim 1, wherein providing the plurality of electrodes comprises implanting electrodes in select locations proximate one or more of a right ventricle, a right atrium, and a left lateral coronary vein of the heart.

4. The method of claim 3, wherein implanting electrodes comprises implanting a bipolar electrode proximate the right ventricle, implanting a bipolar electrode proximate the right atrium, and implanting a unipolar electrode proximate the left lateral coronary vein.

5. The method of claim 1, wherein delivering the electrical stimulus to the heart comprises delivering the electrical stimulus with one or more of the plurality of electrodes.

6. The method of claim 1, further comprising sensing the evoked response using the selected pair of sensing electrodes.

7. A method for delivering therapy to a heart using an implantable medical device, comprising:
implanting a first lead of the implantable medical device proximate a right ventricle of the heart, the first lead having at least one electrode associated therewith;
implanting a second lead of the implantable medical device proximate a right atrium of the heart, the second lead having at least one electrode associated therewith;
implanting a third lead of the implantable medical device through a left lateral coronary vein of the heart proximate a left ventricle of the heart, the third lead having at least one electrode associated therewith;
delivering an electrical stimulus to at least one chamber of the heart;
measuring a polarization potential vector between each of a plurality of combinations of electrodes associated with the first lead, the second lead, the third lead, and a housing of the implantable medical device;
comparing the measured polarization potential vector of each of the plurality of combinations of electrodes; and
selecting a combination of electrodes that yields the lowest measured polarization potential vector for the at feast one chamber of The heart, wherein the selected combination of electrodes is operable for sensing an evoked response to a subsequent electric stimulus delivered to the at least one chamber of the heart.

8. The method of claim 7, wherein the at least one electrode of one or more of the first lead, the second lead, and the third lead comprises both a cathode and an anode.

9. The method of claim 7, wherein measuring the polarization potential vector between each of the plurality of combinations of electrodes comprises measuring two or more of the polarization potential vectors between: one or both of a cathode and an anode of the first lead and one or both of a cathode and an anode of the second lead; one or both of the cathode and the anode of the first lead and one or both of a cathode and an anode of the third lead; and one or both of the cathode and the anode of the second lead and one or both of the cathode and the anode of the third lead.

10. The method of claim 7, further comprising detecting the evoked response in the at least one chamber of the heart using the selected combination of electrodes.

11. The method of claim 7, further comprising delivering a pacing pulse to one or both of the right ventricle and the left ventricle.

12. The method of claim 11, further comprising detecting the evoked response in one or both of the right ventricle and the left ventricle after delivering the pacing pulse.

13. The method of claim 11, wherein delivering the pacing pulse comprises delivering the pacing pulse to the right ventricle via the at least one electrode associated with the first lead.

14. The method of claim 11, wherein delivering the pacing pulse comprises delivering the pacing pulse to the left ventricle via the at least one electrode associated with the second read.

15. The method of claim 7, wherein implanting the first lead comprises implanting the first lead proximate the right ventricle such that a tip electrode of the first lead contacts an interior surface of the right ventricle proximate an apex of the heart.

16. The method of claim 7, wherein implanting the second lead comprises implanting the second lead through a coronary sinus of the heart.

17. The method of claim 7, further comprising implanting one or more electrodes proximate a left atrium of the heart.

18. A method for pacing a ventricle of a heart using an implantable medical device, the method comprising:
selecting a combination of sensing electrodes from a plurality of electrodes that yields a lowest polarization potential vector in response to an electrical stimulus to the ventricle;
delivering a pacing pulse to the ventricle;
measuring one or more parameters of a QRS complex using the selected combination of sensing electrodes; and
detecting capture of the ventricle in response to the pacing pulse by comparing the one or more parameters of the QRS complex to one or more predetermined values.

19. The method of claim 18, wherein measuring the one or more parameters of the QRS complex comprises measuring a width of the QRS complex.

20. The method of claim 18, wherein measuring the one or more parameters of the QRS complex comprises measuring a morphology of the QRS complex.

21. The method of claim 18, wherein the ventricle of the heart is a right ventricle.

22. The method of claim 18, wherein the ventricle of the heart is a left ventricle.

* * * * *

UNITED STATES PATENT AND TRADEMARK OFFICE
CERTIFICATE OF CORRECTION

PATENT NO. : 7,139,610 B2  Page 1 of 1
APPLICATION NO. : 10/132510
DATED : November 21, 2006
INVENTOR(S) : Ferek-Petric It is certified that error appears in the above-identified patent and that said Letters Patent is hereby corrected as shown below:

Column 23, line 66 please change "at feast one" to --at least one--.

Column 24, line 31 please change "second read." to --second lead.--.

Signed and Sealed this

Second Day of October, 2007

JON W. DUDAS
*Director of the United States Patent and Trademark Office*